(12) United States Patent
Akiyama et al.

(10) Patent No.: US 10,124,618 B2
(45) Date of Patent: Nov. 13, 2018

(54) INSPECTION APPARATUS AND METHOD OF INSPECTION

(71) Applicants: Yoshitaka Akiyama, Kanagawa (JP); Yoshinari Suzuki, Kanagawa (JP); Honriku Jo, Kanagawa (JP)

(72) Inventors: Yoshitaka Akiyama, Kanagawa (JP); Yoshinari Suzuki, Kanagawa (JP); Honriku Jo, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 15/425,962

(22) Filed: Feb. 6, 2017

(65) Prior Publication Data

US 2017/0232770 A1    Aug. 17, 2017

(30) Foreign Application Priority Data

Feb. 12, 2016 (JP) .................................. 2016-024723
Dec. 21, 2016 (JP) .................................. 2016-248321

(51) Int. Cl.
| | | |
|---|---|---|
| B41J 29/393 | (2006.01) | |
| B41J 2/21 | (2006.01) | |
| B41J 2/01 | (2006.01) | |
| B41J 2/165 | (2006.01) | |
| G01N 21/84 | (2006.01) | |

(52) U.S. Cl.
CPC .............. *B41J 29/393* (2013.01); *B41J 2/01* (2013.01); *B41J 2/16579* (2013.01); *B41J 2/16585* (2013.01); *B41J 2/2114* (2013.01); *G01N 21/84* (2013.01); *B41J 2029/3935* (2013.01)

(58) Field of Classification Search
CPC .... B41J 29/393; B41J 2/2114; B41J 2/16585; B41J 2/16579; B41J 2/01; B41J 2029/3935; G01N 21/84
See application file for complete search history.

(56) References Cited

U.S. PATENT DOCUMENTS

| | | | |
|---|---|---|---|
| 2008/0186341 A1 | 8/2008 | Hirato | |
| 2016/0075146 A1 | 3/2016 | Akiyama et al. | |

FOREIGN PATENT DOCUMENTS

| | | | |
|---|---|---|---|
| JP | 2000-141624 | 5/2000 | |
| JP | 2008-213471 | 9/2008 | |
| JP | 2011-126059 | 6/2011 | |
| JP | 2012-232499 | * 11/2012 | ................ B41J 2/01 |
| JP | 2016-055627 | 4/2016 | |

* cited by examiner

*Primary Examiner* — Geoffrey Mruk
(74) *Attorney, Agent, or Firm* — Duft & Bornsen, PC

(57) ABSTRACT

An inspection apparatus includes a liquid discharge head and a first light source. The liquid discharge head is configured to discharge a transparent liquid onto a discharged object. The first light source is configured to irradiate a pattern formed by the transparent liquid discharged onto the discharged object with light having a single peak wavelength to cause a difference between brightness and darkness.

16 Claims, 17 Drawing Sheets

INSPECTION APPARATUS AND METHOD OF INSPECTION

CROSS-REFERENCE TO RELATED APPLICATIONS

The present application claims priority under 35 U.S.C. § 119 to Japanese Patent Application No. 2016-024723, filed Feb. 12, 2016 and Japanese Patent Application No. 2016-248321, filed Dec. 21, 2016. The contents of which are incorporated herein by reference in their entirety.

BACKGROUND OF THE INVENTION

1. Field of the Invention

The present invention relates to an inspection apparatus and a method of inspection.

2. Description of the Related Art

Conventionally, in apparatuses that discharge liquids such as inkjet recording apparatuses, it is difficult to perform the discharge detection of transparent liquids, and a method that discharges transparent liquids onto colored liquids is employed. Examples of peripheral techniques related to this method include "a printing apparatus and a method of printing" that can form a print pattern suitable for registration adjustment (refer to Japanese Unexamined Patent Application Publication No. 2000-141624).

This technique according to Japanese Unexamined Patent Application Publication No. 2000-141624 shifts the drive timing of a plurality of groups of print elements to print a print pattern that changes in the color of the overlapped parts of a plurality of basic print patterns.

However, as disclosed in Japanese Unexamined Patent Application Publication No. 2000-141624, when a streak occurs in an object solidly printed with a colored ink by nozzle omission or bent discharge, it is difficult to perform the discharge detection of a transparent ink printed on the streak.

SUMMARY OF THE INVENTION

According to an embodiment, an inspection apparatus includes a liquid discharge head and a first light source. The liquid discharge head is configured to discharge a transparent liquid onto a discharged object. The first light source is configured to irradiate a pattern formed by the transparent liquid discharged onto the discharged object with light having a single peak wavelength to cause a difference between brightness and darkness.

BRIEF DESCRIPTION OF THE DRAWINGS

The accompanying drawings are intended to depict exemplary embodiments of the present invention and should not be interpreted to limit the scope thereof. Identical or similar reference numerals designate identical or similar components throughout the various drawings.

DESCRIPTION OF THE EMBODIMENTS

Figure 1:
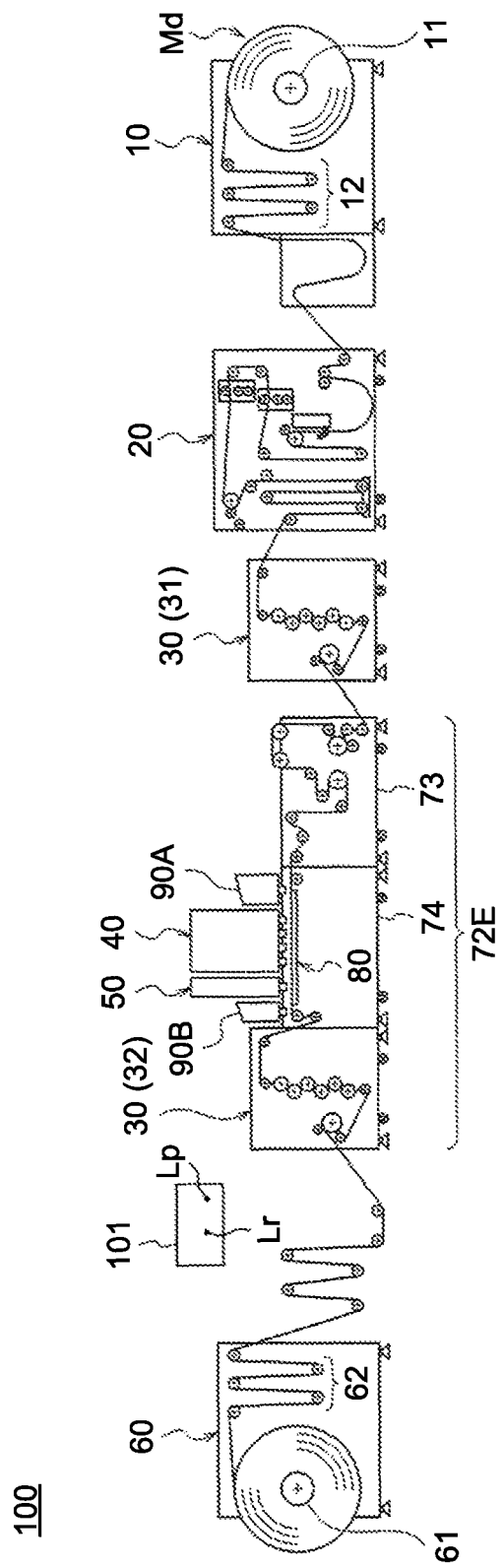
FIG. 1 is a schematic side view of an example of an image forming apparatus that includes an inspection apparatus according to an embodiment of the present invention and performs image formation on a discharged object to be inspected.

The terminology used herein is for the purpose of describing particular embodiments only and is not intended to be limiting of the present invention.

As used herein, the singular forms "a", "an" and "the" are intended to include the plural forms as well, unless the context clearly indicates otherwise.

In describing preferred embodiments illustrated in the drawings, specific terminology may be employed for the sake of clarity. However, the disclosure of this patent specification is not intended to be limited to the specific terminology so selected, and it is to be understood that each specific element includes all technical equivalents that have the same function, operate in a similar manner, and achieve a similar result.

An embodiment of the present invention will be described in detail below with reference to the drawings.

An object of an embodiment is to provide an inspection apparatus and a method of inspection that can appropriately detect the faulty discharge of a liquid discharge head that discharges a transparent liquid onto a discharged object.

FIG. 1 is a schematic side view of an example of an image forming apparatus 100 that includes an inspection apparatus according to the embodiment of the present invention and performs image formation on a discharged object to be inspected. The present embodiment will be described assuming that a liquid discharge head is a recording head or an ink head that discharges ink droplets of four colors of black K, cyan C, magenta M, and yellow Y or a transparent posttreatment liquid onto a recording medium as the discharged object. In this regard, other than that, the liquid discharge head may be a configuration of a type handling green G, red R, and light cyan LC, a type corresponding to other colors, or a type handling only black K.

Although the present embodiment assumes a case using rolled paper Md that is continuous stationery wound in a rolled manner as the recording medium to be the discharged object, the recording medium is not limited to the continuous stationery. In other words, the recording medium that can form images using the image forming apparatus includes cut paper, plain paper, high-quality paper, thin paper, thick paper, recording paper, a transparency, a synthetic resin film, a metallic thin film, and other sheet members that can form images thereon with inks or the like. For information, the rolled paper in this example is continuous stationery indicating continuous form paper or a continuous form.

Referring to FIG. 1, the image forming apparatus 100 includes a feeder 10 that feeds the rolled paper Md, a pretreatment unit 20 that pretreats the fed rolled paper Md, and a drying unit 30 that dries the pretreated rolled paper Md. The image forming apparatus 100 also includes an image forming unit 40 that forms images on the surface of the rolled paper Md, a posttreatment unit 50 that posttreats the image-formed rolled paper Md, and a carry-out unit 60 that carries out the posttreated rolled paper Md. The image forming unit 40, the posttreatment unit 50, and maintenance-and-restoration units 90A and 90B are arranged on a casing 74 of a printer engine 72E. The casing 74 as an inkjet printer main body includes a conveying unit 80 including a conveying belt. A scanner 101 provided on the downstream side of the drying unit 30 forms an inspection apparatus that automatically inspects a discharge detection pattern image-formed on the rolled paper Md together with discharge heads provided in the image forming unit 40 and the posttreatment unit 50. A light source held by an inspection stage through an illumination mounting tool including an illumination operating unit as a separate configuration from the image forming apparatus 100 also forms an inspection apparatus that visually inspects the discharge detection pattern together with the discharge heads similarly. These inspection apparatuses will be described below in detail including their detailed configurations.

The image forming unit 40, the posttreatment unit 50, the maintenance-and-restoration units 90A and 90B, a casing 73, the casing 74, and a drying unit 32 for posttreatment correspond to the printer engine 72E. The image forming apparatus 100 further includes a controller 70 that controls the operation of the apparatus as described below with reference to FIG. 11.

The image forming apparatus 100 according to the present embodiment feeds the rolled paper Md by the feeder 10 and pretreats and dries the surface of the rolled paper Md by the pretreatment unit 20 and the drying unit 30. The image forming apparatus 100 forms images on the surface of the rolled paper Md after being pretreated and dried by the image forming unit 40. Further, the image forming apparatus 100 in the present embodiment posttreats the image-formed rolled paper Md by the posttreatment unit 50. Subsequently, the image forming apparatus 100 winds the rolled paper Md by the carry-out unit 60 and discharges or carries out the rolled paper Md to the outside of the apparatus.

The following specifically describes the components of the image forming apparatus 100. The image forming apparatus 100 itself can be a configuration that does not include any one or more of the pretreatment unit 20 and the like described below in accordance with the type of the recording medium on which an image will be formed.

The feeder 10 is a unit that conveys the recording medium to the pretreatment unit 20 and the like. The feeder 10 in the present embodiment includes a paper feeding unit 11 and a plurality of conveying rollers 12. The feeder 10 feeds and moves the rolled paper Md held by being wound around a paper feeding roll of the paper feeding unit 11 using the conveying rollers 12 and the like to convey the rolled paper Md to the pretreatment unit 20 and the like described below using a platen and the like.

The pretreatment unit 20 is a unit that treats the recording medium before the image is formed and in the present embodiment pretreats the surface of the rolled paper Md fed by the feeder 10 with a pretreatment liquid. In this example, the pretreatment is treatment that uniformly applies the pretreatment liquid having a function of flocculating an ink to the surface of the rolled paper Md. With this treatment, when an image is formed on a recording medium that is paper for inkjet exclusive use or other than the paper for inkjet exclusive use, the image forming apparatus 100 can apply the pretreatment liquid having the function of flocculating the ink to the surface of the recording medium using the pretreatment unit 20 before forming the image on the recording medium.

Consequently, the image forming apparatus 100 can reduce the occurrence of quality problems such as the blur, the density, the tone, and the set-off of the formed image and problems concerning waterproofness, weatherproofness, and other image robustness. Consequently, the quality of an image to be formed subsequently can be improved.

Figure 2:
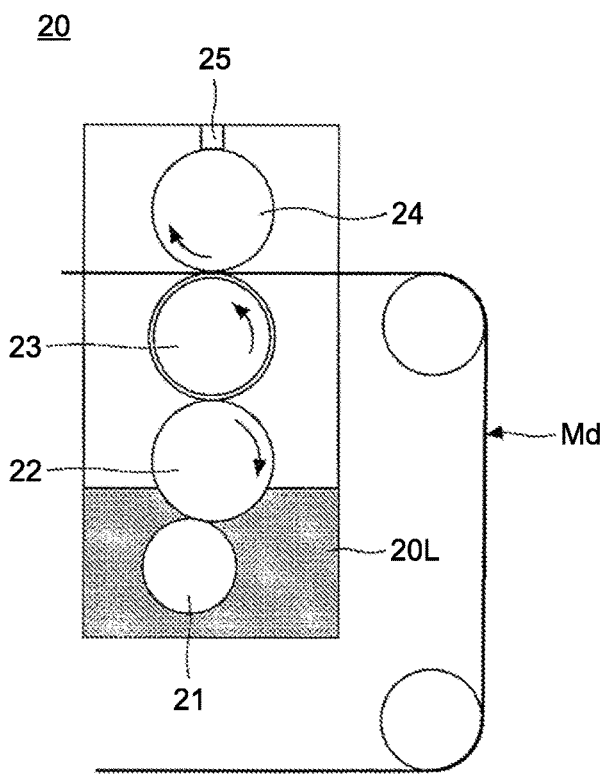
FIG. 2 is a schematic configuration diagram of an example of a pretreatment unit of the image forming apparatus in FIG. 1.

FIG. 2 is a schematic configuration diagram of an example of the pretreatment unit 20 of the image forming apparatus 100. The following describes an example using roll coating as the pretreatment unit 20. As illustrated in FIG. 2, the pretreatment unit 20 in the present embodiment applies a stored pretreatment liquid 20L to the surface of the rolled paper Md fed into the pretreatment unit 20 by the feeder 10.

Specifically, the pretreatment unit 20 first moves and transfers the pretreatment liquid 20L to the surface of an application roller 23 in a thin film shape by a stirring roller 21 for supply and a thin film forming roller 22 for transfer. Next, the pretreatment unit 20 presses the application roller 23 against a rotating platen roller 24 to rotate the application roller 23. In this process, the pretreatment unit 20 conveys the rolled paper Md to a gap between the application roller 23 and the platen roller 24, thereby applying the pretreatment liquid 20L to the surface of the rolled paper Md.

The pretreatment unit 20 controls at least either of nip pressure indicating pressure acting on a position at which the application roller 23 and the platen roller 24 come into contact with each other or the rotation speed of the application roller 23 and the platen roller 24 when the pretreatment liquid 20L is applied using a pressure adjustment apparatus 25. With this control, the pretreatment unit 20 changes the nip pressure using the pressure adjustment apparatus 25 while changing the rotation speed of the application roller 23 and the like, whereby the film thickness, the liquid amount, the adhesion amount, and the application amount such as a dried adhesion amount of the pretreatment liquid 20L can be changed and controlled. Consequently, the pretreatment liquid 20L can be applied to the surface of the rolled paper Md with an application amount appropriate for the subsequent image formation and posttreatment.

The drying unit 30 is a unit that dries the recording medium by heating or the like. In the present embodiment, the drying unit 30 includes a drying unit 31 for pretreatment that dries the rolled paper Md pretreated by the pretreatment unit 20 and a drying unit 32 for posttreatment that dries the rolled paper Md posttreated by the posttreatment unit 50.

For the drying unit 31 for pretreatment, heat rollers 311 to 316 can be used, for example, as described below with reference to FIG. 3. Specifically, the drying unit 31 for pretreatment heats the heat rollers 311 to 316 up to 40° C. to 110° C., for example, thereby causing the surface of the rolled paper Md to which the pretreatment liquid 20L has been applied to be in contact or the like with the heat rollers 311 to 316. With this operation, the drying unit 31 for pretreatment can heat the surface of the rolled paper Md to which the pretreatment liquid 20L has been applied by the heat rollers 311 to 316, evaporate water in the pretreatment liquid 20L, and dry the pretreatment liquid 20L on the rolled paper Md.

Figure 3:
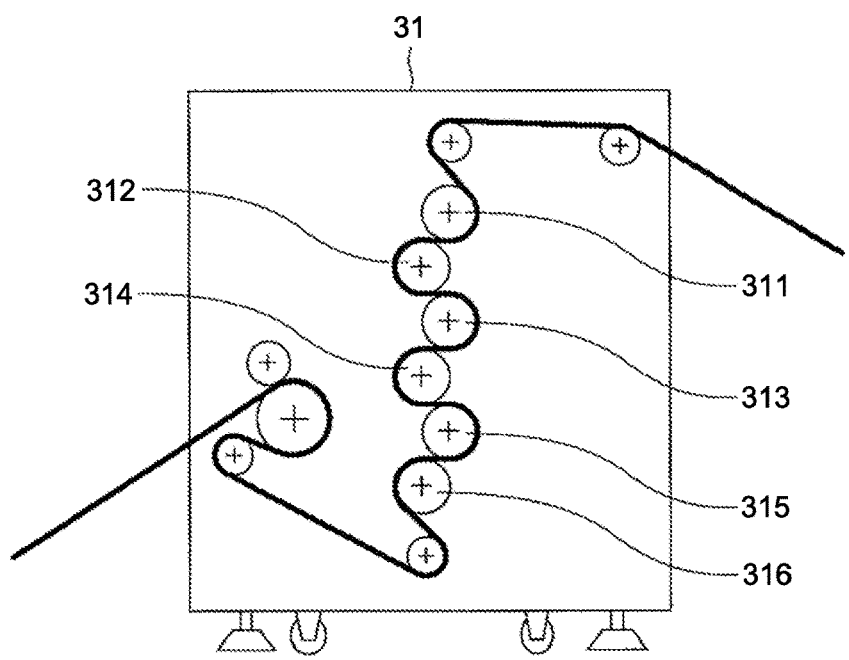
FIG. 3 is a schematic configuration diagram illustrating an example of a drying unit of the image forming apparatus in FIG. 1.

FIG. 3 is a schematic configuration diagram illustrating an example of the drying unit 30 of the image forming apparatus 100. In the drying unit 31 for pretreatment of the drying unit 30, the heat rollers 311 to 316 are preferably provided in a multistage manner as illustrated in FIG. 3 in order to enhance a drying effect. When drying intensity is weakened in such a configuration, a heat roller temperature is decreased. The heat roller temperature may be about 40° C. to 80° C., for example. Further, only the heat rollers 311 and 312 are heated, for example, whereas the other heat rollers 313 to 316 are not heated, for example. In contrast, the number of the heat rollers used or the heat roller temperature is increased, whereby the drying intensity can be enhanced.

For information, although an example in which the heat roller temperature and the number of the heat rollers used are controlled has been described in this example, even only either of them can control the drying intensity. Thus, a combination of the heat roller temperature and the number of the heat rollers used can control the drying intensity.

The drying unit 31 for pretreatment of the drying unit 30 is not limited to the heat rollers 311 to 316. In other words, for the drying unit 31 for pretreatment, infrared drying, microwave drying, hot-air drying, and other drying techniques can be used. For the drying unit 31 for pretreatment, a drying technique obtained by combining a plurality of drying techniques may be used. Further, for the drying unit 31 for pretreatment, as a preheating process, the rolled paper Md may be heated before the pretreatment unit 20 applies the pretreatment liquid 20L.

The configuration of the drying unit 32 for posttreatment is similar to the configuration of the drying unit 31 for pretreatment, and a description thereof is omitted.

The image forming unit 40 is a unit that forms images on the rolled paper Md as the recording medium. The image forming unit 40 in the present embodiment discharges ink droplets onto the rolled paper Md dried by the drying unit 30 to form images on the surface of the rolled paper Md.

Figure 4A:
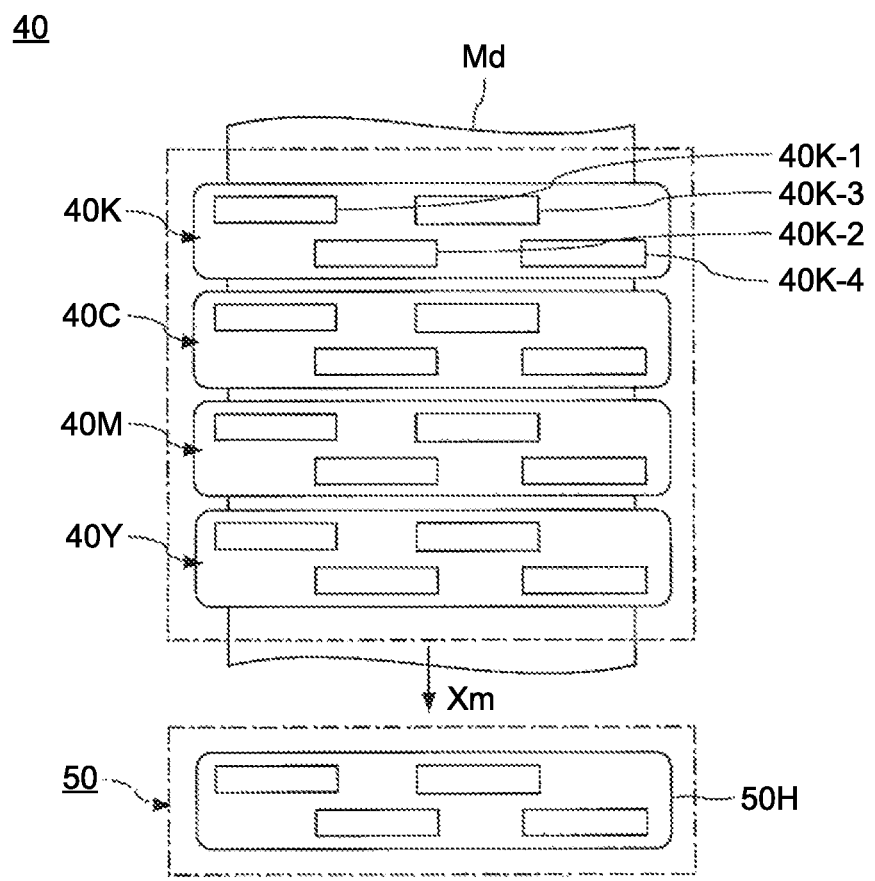
FIG. 4A is a schematic plan view illustrating an arrangement configuration of the entire image forming unit.
Figure 4B:
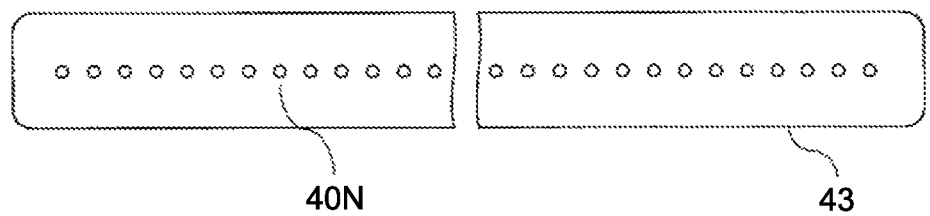
FIG. 4B is a schematic plan view illustrating the main part of the image forming unit in an enlarged view.

FIGS. 4A and 4B are illustrative diagrams illustrating a case in which a full-line type liquid discharge head is used as an example of the image forming unit 40 and a posttreatment liquid discharge unit of the image forming apparatus 100. FIG. 4A is a schematic plan view illustrating an arrangement configuration of the entire image forming unit 40, and FIG. 4B is a schematic plan view illustrating the main part of the image forming unit 40 in an enlarged view.

As illustrated in FIG. 4A, for the image forming unit 40 in the present embodiment, the full-line type liquid discharge head can be used. In other words, the image forming unit 40 arranges four discharge heads 40K, 40C, 40M, and 40Y corresponding to black K, cyan C, magenta M, and yellow Y, respectively, from the upstream side in a conveyance direction Xm of the rolled paper Md as the recording medium.

In FIG. 4A, the discharge head 40K of black K in the present embodiment arranges four head units 40K-1, 40K-2, 40K-3, and 40K-4 in a staggered manner in a direction orthogonal to the conveyance direction Xm of the rolled paper Md. With this arrangement, the image forming unit 40 can form images in the entire area in the width direction as the direction orthogonal to the conveyance direction Xm in an image forming area as a print area of the rolled paper Md. The rolled paper Md is conveyed in the conveyance direction Xm by a conveying belt 81, and the head units 40K-1, 40K-2, 40K-3, and 40K-4 move relative to the rolled paper Md in a direction opposite to its conveyance direction Xm. The configurations of the other discharge heads 40C, 40M, and 40Y are similar to the configuration of the discharge head 40K of black K, and descriptions thereof are omitted.

FIG. 4B is an enlarged plan view of the head unit 40K-1 of the discharge head 40K of black K of the image forming unit 40. The head unit 40K-1 in the present embodiment includes a plurality of discharge ports 40N on a nozzle face corresponding to an outer surface of a nozzle plate 43 in FIG. 5A described below. The discharge ports 40N correspond to nozzles or print nozzles and are arranged in a row in the longitudinal direction of the head unit 40K-1 to form a nozzle row. The head unit 40K-1 may include a plurality of nozzle rows. Although the example in FIG. 4A forms a liquid discharge head that has two nozzle rows and discharges droplets of one line by two adjacent head units, the liquid discharge head may have other shapes; the liquid discharge head may be configured by connecting a plurality of head units and arranging them in a row, or the liquid discharge head may have a configuration in which one head unit in which one line extending in the width direction of the rolled paper Md corresponds to one nozzle corresponds to one head, for example. For information, FIG. 4A also illustrates a discharge head 50H of the posttreatment unit 50 described below.

The discharge heads 40K, 40C, 40M, and 40Y are mounted on a carriage 46 described below with reference to FIG. 7 to be a first discharge unit discharging colored ink droplets.

Figure 5A:
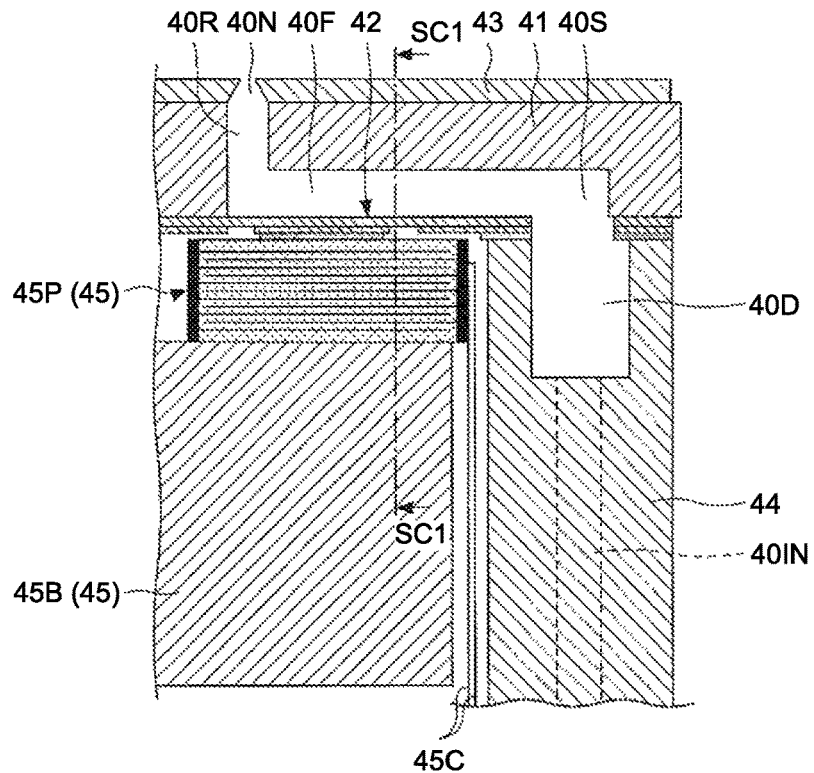
FIG. 5A is a longitudinal sectional view of a liquid chamber of a liquid discharge head.
Figure 5B:
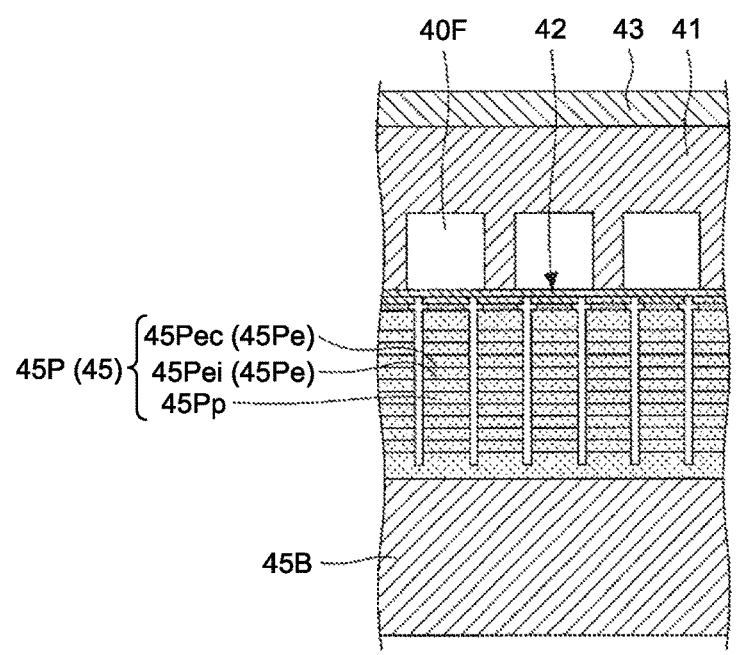
FIG. 5B is a transverse sectional view of the liquid chamber of the liquid discharge head in the SC1-SC1 direction in FIG. 5A indicating an arrangement direction of discharge ports.

FIGS. 5A and 5B are schematic sectional views illustrating an example of the image forming unit 40 and the posttreatment liquid discharge unit of the image forming apparatus 100. FIG. 5A is a longitudinal sectional view of a liquid chamber 40F of a liquid discharge head, and FIG. 5B is a transverse sectional view of the liquid chamber 40F of the liquid discharge head in the SC1-SC1 direction in FIG. 5A indicating the arrangement direction of the discharge ports 40N.

Referring to FIG. 5A, the discharge head 40K as one of the liquid discharge heads of the image forming unit 40 according to the embodiment of the present invention includes a channel plate 41 forming a channel for an ink to be discharged and a vibration plate 42 connected to a lower face of the channel plate 41 in an inner direction of the discharge head 40K. The discharge head 40K also includes a nozzle plate 43 connected to an upper face of the channel plate 41 in an outer direction of the discharge head 40K and a frame member 44 holding a peripheral part of the vibration plate 42. The discharge head 40K includes a pressure generating unit 45 by an actuator unit for deforming the vibration plate 42.

The discharge head 40K according to the present embodiment stacks the channel plate 41, the vibration plate 42, and the nozzle plate 43, thereby forming a nozzle communication channel 40R as a channel to communicate with the discharge port 40N of the nozzle and the liquid chamber 40F. The discharge head 40K further stacks the frame member 44, thereby forming an ink inflow port 40S for supplying the ink to the liquid chamber 40F, a common liquid chamber 40D that supplies the ink to the liquid chamber 40F, and the like.

Further, the discharge head 40K can bend the vibration plate 42 using the pressure generating unit 45. With this bending, the discharge head 40K can change the volume of the liquid chamber 40F and change pressure acting on the ink within the liquid chamber 40F. Consequently, the discharge head 40K can discharge the ink from the discharge port 40N.

In addition, the frame member 44 in the present embodiment is formed with a housing part that houses the pressure generating unit 45, a recess to be the common liquid chamber 40D, and an ink supply port 40IN for supplying the ink to the common liquid chamber 40D from the outside of the discharge head.

For the pressure generating unit 45, electromechanical transducer elements can be used. The pressure generating unit 45 in the present embodiment includes piezoelectric elements 45P as the electromechanical transducer elements, a base substrate 45B that connects and fixes the piezoelectric elements 45P, and supports arranged in gaps between adjacent piezoelectric elements 45P. The pressure generating unit 45 includes an FPC cable 45C for connecting the piezoelectric elements 45P to a driver circuit by a driver IC, for example.

As illustrated in FIG. 5B, for the piezoelectric element 45P, a stacked piezoelectric element (PZT) in which a piezoelectric material 45Pp and an internal electrode 45Pe are alternately stacked can be used. The internal electrode 45Pe includes a plurality of individual electrodes 45Pei and a plurality of common electrodes 45Pec. The internal electrode 45Pe in the present embodiment alternately connects the individual electrode 45Pei and the common electrode 45Pec to an end face of the piezoelectric material 45Pp. Further, the piezoelectric element 45P in the present embodiment uses the d33 direction as the piezoelectric direction of the piezoelectric material 45Pp. With this configuration, the pressure generating unit 45 can pressurize or depressurize the ink within the liquid chamber 40F using a piezoelectric effect indicating the displacement in the d33 direction of the piezoelectric element 45P. The pressure generating unit 45 may pressurize or depressurize the ink within the liquid chamber 40F using displacement in the d31 direction of the piezoelectric element 45P or arrange piezoelectric elements in a row for one discharge port 40N. The supports may be formed simultaneously with the piezoelectric elements 45P by dividing the piezoelectric elements 45P. In other words, the discharge head 40K can use piezoelectric element members as the supports by applying no voltage to the piezoelectric elements 45P.

The following specifically describes a pulling ejection/pushing ejection operation when the discharge head 40K discharges the ink from the discharge ports 40N of the nozzles.

The discharge head 40K in the present embodiment first decreases voltage being applied to the piezoelectric elements 45P of the pressure generating unit 45 from a reference potential to shrink the piezoelectric elements 45P in their stacking direction. The discharge head 40K bends the vibration plate 42 by the shrinkage of the piezoelectric elements 45P. In this process, the discharge head 40K expands the volume of the liquid chamber 40F by the bending of the vibration plate 42. With this expansion, the discharge head 40K can cause the ink to flow into the liquid chamber 40F from the common liquid chamber 40D.

Next, the discharge head increases the voltage being applied to the piezoelectric elements 45P to elongate the piezoelectric elements 45P in the stacking direction. The discharge head 40K deforms the vibration plate 42 toward the discharge ports 40N by the elongation of the piezoelectric elements 45P. In this process, the discharge head 40K reduces the volume of the liquid chamber 40F by the deformation of the vibration plate 42. With this volume reduction, the discharge head 40K can apply pressure to the ink within the liquid chamber 40F. The discharge head 40K can discharge and eject the ink from the discharge ports 40N of the nozzles by pressurizing the ink.

Subsequently, the discharge head 40K restores the voltage being applied to the piezoelectric elements 45P to the reference potential to restore the vibration plate 42 to the initial position. In this process, the discharge head 40K reduces the pressure within the liquid chamber 40F by the expansion of the liquid chamber 40F to charge and replenish the ink within the liquid chamber 40F from the common liquid chamber 40D. Further, after the vibration of the meniscus face of the discharge ports 40N of the nozzles attenuates and stabilizes, the discharge head 40K shifts to operation for the next ink discharge and repeats the above-described operation.

A method for driving the discharge head 40K that can be used in the present embodiment is not limited to the pulling ejection/pushing ejection operation. In other words, the method for driving the discharge head 40K can perform pulling ejection, pushing ejection, and the like by controlling the driving waveform of the voltage to be applied to the piezoelectric elements 45P.

From the foregoing, the image forming apparatus 100 according to the present embodiment can form black-and-white or full-color images in the entire area of the image forming area by one conveying operation of the rolled paper Md using the four discharge heads 40K, 40C, 40M, and 40Y of the image forming unit 40.

To determine the presence or absence of the necessity of maintenance apart from during printing such as before printing, test patterns are created. As the test patterns, a test pattern for detecting discharge clogging of the discharge heads 40K, 40C, 40M, and 40Y of the respective colors of the image forming unit 40 and a test pattern for detecting discharge clogging of the head of the posttreatment unit 50 are created. For the detection of the discharge clogging of the posttreatment unit 50, the image forming unit 40 preferably forms a monochrome solid image with any one color, for example.

The pressure generating unit 45 that can be used in the present embodiment is not limited to the piezoelectric elements 45P. In other words, for the pressure generating unit 45, what is called a thermal type one may be used that heats the ink within the liquid chamber 40F using a heating resistor to generate air bubbles as disclosed in Japanese Unexamined Patent Application Publication No. S61-59911, for example. For the pressure generating unit 45, what is called an electrostatic type one may be used that arranges a vibration plate and an electrode on the wall faces of the liquid chamber 40F so as to face each other and deforms the vibration plate through an electrostatic force generated between the vibration plate and the electrode as disclosed in Japanese Unexamined Patent Application Publication No. H06-71882, for example.

The posttreatment unit 50 is a unit that treats the recording medium after the image has been formed. The posttreatment unit 50 in the present embodiment posttreats the surface of the rolled paper Md on which the image has been formed by the image forming unit 40 with a posttreatment liquid. This posttreatment is treatment to discharge the posttreatment liquid described below onto the rolled paper Md and to accumulate the posttreatment liquid. The posttreatment liquid is formed in a shape such as a spot-like shape or a banded shape. With this treatment, the image-formed rolled paper Md can be improved in rubfastness and glossiness, and in addition, can be improved also in storage stability such as waterproofness, lightfastness, and gas resistance.

Figure 6A:
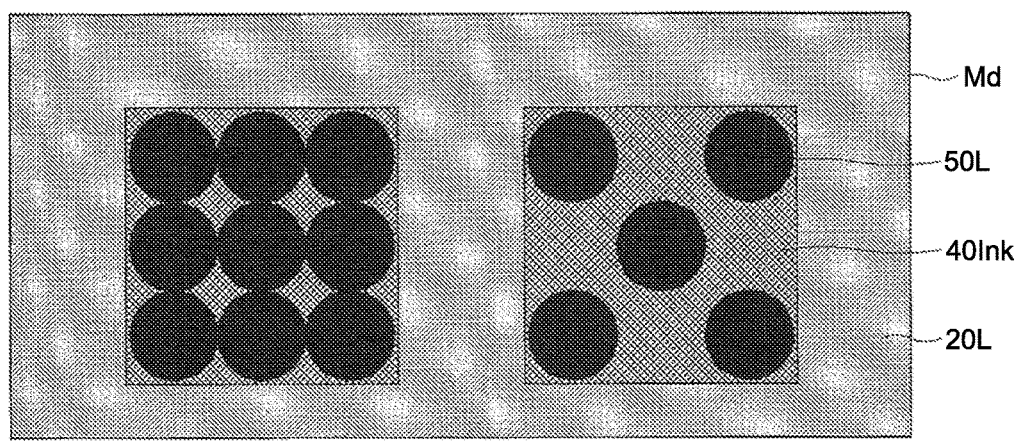
FIG. 6A is a top view of the image-formed rolled paper.
Figure 6B:
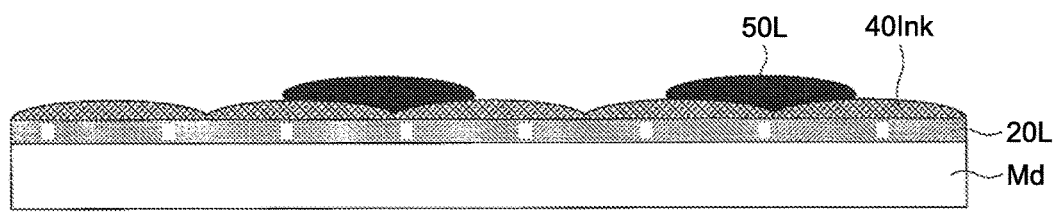
FIG. 6B is a sectional view in a side longitudinal direction of the image-formed rolled paper.

FIGS. 6A and 6B are illustrative diagrams illustrating an example of the rolled paper Md after image formation has been performed by the image forming apparatus 100. FIG. 6A is a top view of the image-formed rolled paper Md, and FIG. 6B is a sectional view in a side longitudinal direction of the image-formed rolled paper Md.

Referring to FIG. 6A, this example illustrates how the pretreatment liquid 20L has been applied to the surface of the rolled paper Md at the start of the posttreatment by the posttreatment unit 50 and an ink 40Ink for image formation has been further discharged, for example. The posttreatment unit 50 performs treatment to discharge and accumulate transparent droplets 50L as the posttreatment liquid onto the image-formed rolled paper Md as the posttreatment so as to be similar in the following. How the transparent droplets 50L are accumulated on the ink 40Ink is clear by referring to FIG. 6B. The transparent droplets 50L are discharged onto an area at least smaller than that of the pretreatment liquid 20L to be accumulated. In this sectional view, the ink 40Ink is discharged onto the entire surface, whereas the transparent droplets 50L are discharged onto an area smaller than the area of the ink 40Ink to be accumulated.

Although FIG. 6A and FIG. 6B illustrate the transparent droplets 50L formed in a spot-like shape, the transparent droplets 50L may be a banded shape in a direction orthogonal to the section instead thereof.

The transparent droplets 50L may be discharged onto an area smaller than the image-formed surface area to be accumulated at least in the image-formed part of the rolled paper Md, and in a non-image-formed part, the transparent droplets 50L may be discharged or are not necessarily discharged.

As a method of posttreatment, the posttreatment liquid is preferably discharged onto only a specific part of the image-formed area of the rolled paper Md to be accumulated. The posttreatment unit 50 further preferably changes a discharge amount as the application amount of the posttreatment liquid and a method of discharge as a method of application based on the type, the permeability, the glossiness, and the resolution of the recording medium such as the rolled paper Md and an application amount as the liquid amount of the pretreatment liquid applied by the pretreatment unit 20.

The posttreatment unit 50 according to the present embodiment can discharge the posttreatment liquid with a desired discharge amount so as to be a desired spot-like shape or a desired banded shape at any area as any location using a discharge head similar to those of the image forming unit 40 illustrated in FIG. 4.

Specifically, the posttreatment unit 50 can select firstly discharging the post treatment liquid onto the entire area of an image-formable range, secondly discharging the post treatment liquid onto an image-formed area, thirdly discharging the post treatment liquid onto only an area of an image-formed part to be a dot discharge part, and the like to the rolled paper Md. The posttreatment unit 50 can select fourthly discharging the post treatment liquid onto the periphery of the image-formed area as a wider area than the image-formed area of the rolled paper Md by +1 dot, 2 dots or more, or the like. Further, the posttreatment unit 50 can discharge the posttreatment liquid onto an n % area so as to be a spot-like shape or a banded shape to a selected area onto which the posttreatment liquid is to be discharged. In some illustrative cases, the n % can be 5 to 50%. The n % can be a value preset by experiment, numerical calculation, or the like.

As a method for discharging the transparent droplets 50L, the posttreatment unit 50 according to the present embodiment can select firstly discharging the transparent droplets 50L based on print Duty, secondary discharging the transparent droplets 50L based on the droplet amount of the transparent droplets 50L to be discharged, and the like. In this process, the posttreatment unit 50 may calculate the print Duty and the droplet amount of the transparent droplets 50L from input information such as print image data and determine the method for discharging the transparent droplets 50L based on the calculated print Duty and the like.

Consequently, the image forming apparatus 100 according to the present embodiment can discharge and accumulate the posttreatment liquid only onto the specific part of the image-formed area using the posttreatment unit 50 compared with a case in which the posttreatment liquid is discharged and applied onto the entire surface of the recording medium such as the rolled paper Md. Consequently, the image forming apparatus 100 according to the present embodiment can reduce a time required for the posttreatment, especially a time required for drying the posttreatment liquid. In addition, the liquid amount of the posttreatment liquid required for the posttreatment can be reduced. Consequently, costs required for the posttreatment can be reduced.

The method of posttreatment by the posttreatment unit 50 is not limited to a particular method and may be selected as appropriate in accordance with the type of the posttreatment liquid. The method of posttreatment by the posttreatment unit 50 more preferably uses a method similar to the method for discharging inks by the image forming unit 40 in view of the downsizing of the apparatus and the storage stability of the posttreatment liquid. Consequently, similarly also in terms of configuration, as described with reference to FIG. 4A, the posttreatment liquid discharge unit includes a plurality of discharge ports 50N of nozzles or print nozzles on a nozzle face. A discharge head 50H as the posttreatment liquid discharge unit including the nozzle plate 43 is mounted on a carriage 56 described below with reference to FIG. 7. This discharge head 50H is a second discharge unit discharging the transparent droplets 50L as the posttreatment liquid.

When the posttreatment liquid is discharged, a water soluble organic solvent, which is a wetting agent used in the method for discharging inks by the image forming unit 40, is preferably contained in an appropriate amount.

The posttreatment unit 50 according to the present embodiment preferably has a dry adhesion amount of the posttreatment liquid of 0.5 $g/m^2$ to 10 $g/m^2$.

The posttreatment unit 50 according to the present embodiment can use a treatment liquid containing a component that can form a transparent protective layer on the rolled paper Md as the recording medium, as the posttreatment liquid. The treatment liquid containing the component that can form the transparent protective layer is a treatment liquid containing a water-dispersible resin containing a resin, a water-soluble organic solvent as a wetting agent, a penetrant, a surfactant, water, and other components as needed, for example. The posttreatment liquid may be a resin composition or a thermoplastic resin containing a component polymerized by UV irradiation. Further, the posttreatment liquid is preferably a thermoplastic resin emulsion in order to improve glossiness and fixability. Consequently, the posttreatment unit 50 can increase the glossiness of the surface of the image-formed rolled paper Md or protect the surface of the rolled paper Md with a resin layer in accordance with the method of discharge as the method of application.

Using the posttreatment unit 50 described above can prevent an ink image on the rolled paper Md from being stripped and separated caused by the surface of the image-formed rolled paper Md getting rubbed against another object such as another recording medium and improve rubfastness as rubbing resistance. Further, the occurrence of quality problems such as the blur, the density, the tone, the glossiness, and the set-off of the formed image and problems concerning waterproofness, weatherproofness, and other image robustness can be reduced.

The maintenance-and-restoration units 90A and 90B are maintenance units that perform the maintenance and restoration of the image forming unit 40 and the posttreatment unit 50. When the discharge heads 40K, 40C, 40M, and 40Y of the first discharge unit and the discharge head 50H of the second discharge unit described with reference to FIG. 4A are used for a long time, they may be clogged with the inks and the posttreatment liquid. Given this situation, other than during printing such as before printing, a maintenance-and-restoration operation of cleaning and maintenance is preferably performed. The following discloses an example of the maintenance-and-restoration units 90A and 90B when line type liquid discharge heads are used for the image forming unit 40 and the posttreatment unit 50.

Figure 7:
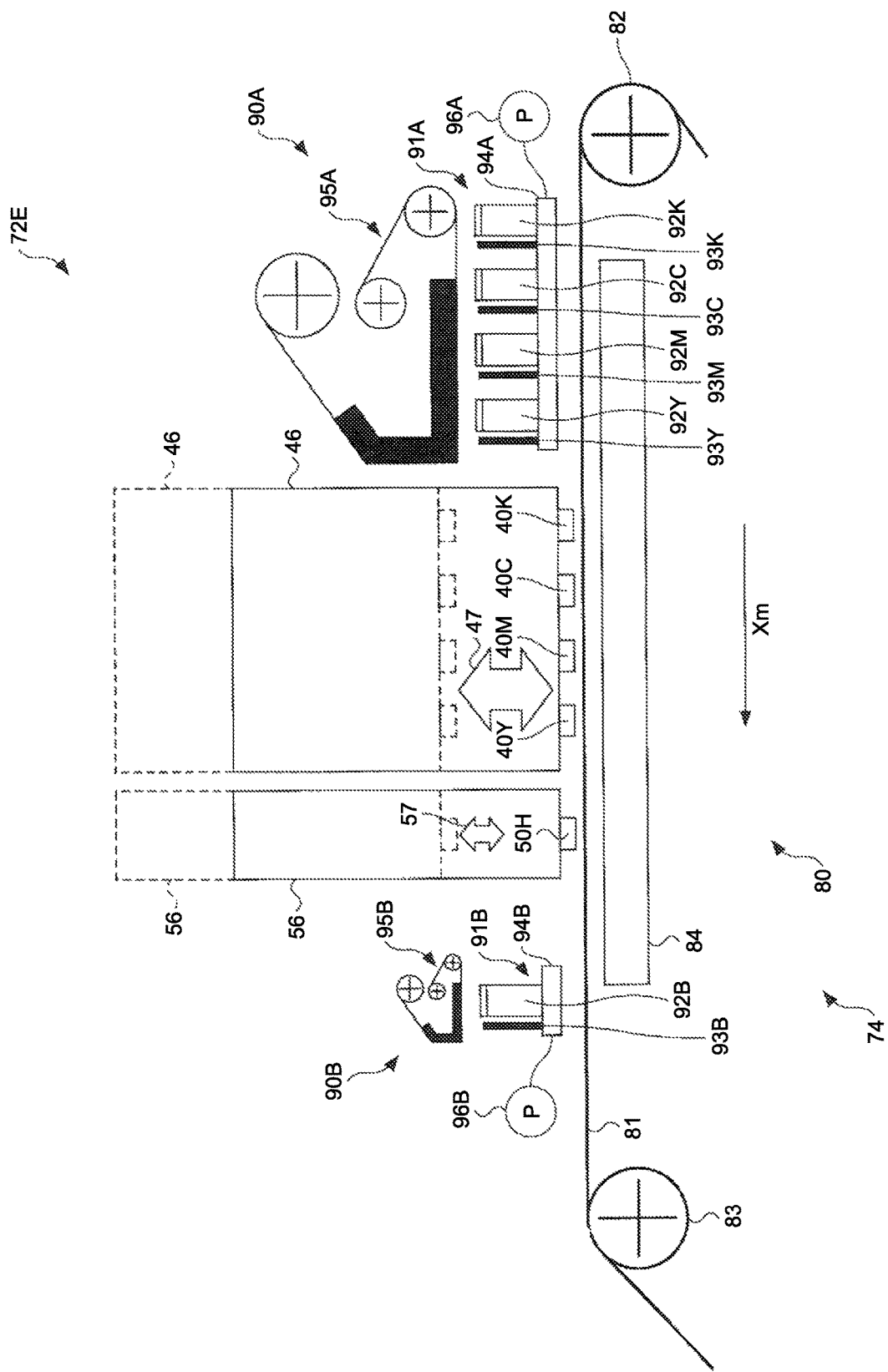
FIG. 7 is a diagram illustrating a schematic structure of the image forming unit and the posttreatment liquid discharge unit of the image forming apparatus in FIG. 1 and their maintenance-and-restoration units.

FIG. 7 is a diagram illustrating a schematic structure of the image forming unit 40 and the posttreatment liquid discharge unit of the image forming apparatus 100 and their maintenance-and-restoration units 90A and 90B. Referring to FIG. 7, the discharge heads 40K, 40C, 40M, and 40Y as the first discharge unit of the image forming unit 40 and the discharge head 50H as the second discharge unit of the posttreatment unit 50 are configured to be movable up and down and are arranged facing the conveying belt 81 as the conveying unit. The conveying belt 81 conveys the rolled paper Md in the arrowed conveyance direction Xm. The maintenance-and-restoration unit 90A is provided upstream in the conveyance direction Xm of the rolled paper Md on the right side in FIG. 7, whereas the maintenance-and-restoration unit 90B is provided downstream in the conveyance direction of the rolled paper Md on the left side in FIG. 7.

The discharge heads 40K, 40C, 40M, and 40Y as the first discharge unit of the image forming unit 40 are installed in the carriage 46, whereas the discharge head 50H as the second discharge unit of the posttreatment liquid discharge unit is installed in the carriage 56.

The carriages 46 and 56 move up and down and can thereby move between a position close to the conveying unit 80 illustrated in FIG. 7, that is, a recording position as a printing position that discharges the inks and the liquid of the posttreatment liquid and a separated position as a position separated from the conveying unit 80 indicated as the dotted-line part. This separated position is a maintenance position at which both the image forming unit 40 and the posttreatment unit 50 perform maintenance by the maintenance-and-restoration units 90A and 90B, is a waiting position waiting for a next operation, and a restoration position at which maintenance is performed.

To perform the up-and-down move, the carriages 46 and 56 are supported by carriage position moving units 47 and 57, respectively, for example. By moving the carriage position moving units 47 and 57, the positions of the carriages 46 and 56 move up and down relative to the casing 74 of the printer engine 72E including the conveying belt 81. Although FIG. 7 indicates the carriage position moving units 47 and 57 by arrows, a moving mechanism combining rails and rollers in structure may be used, or the carriages 46 and 56 may be lifted using arms or the like.

In the conveying unit 80, the conveying belt 81 is stretched between a drive roller 83 rotated by a motor and a driven roller 82 to be circled, and the rolled paper Md is conveyed in the conveyance direction Xm by the circling of the conveying belt 81 supported by a support member 84. In this process, the support member 84 may include a suction unit or an electrostatic attraction unit for attracting the rolled paper Md during conveyance.

The maintenance-and-restoration unit 90A includes an engaging unit 91A and a cleaning unit 95A, whereas the maintenance-and-restoration unit 90B similarly includes an engaging unit 91B and a cleaning unit 95B.

The engaging unit 91A reciprocates relative to a facing area facing the discharge heads 40K, 40C, 40M, and 40Y of the image forming unit 40 at the separated position and is selectively engaged with the discharge heads 40K, 40C, 40M, and 40Y when maintenance is performed. The engaging unit 91B reciprocates relative to a facing area facing the discharge head 50H of the posttreatment liquid discharge unit at the separated position and is engaged with the discharge head 50H when maintenance is performed.

The maintenance-and-restoration units 90A and 90B are similar in structure except the number of cap parts and the inks and the liquid of the posttreatment liquid to be received, and the following describes the maintenance-and-restoration unit 90B of the posttreatment unit 50 to be controlled and omits a description of the maintenance-and-restoration unit 90A. Consequently, the same components are denoted by the same reference numerals with the symbols attached to the ends of the numerals replaced.

The engaging unit 91B includes a cap part 92B, a wiper 93B, and a fixing member 94B that fixes the cap part 92B and the wiper 93B. The cap part 92B is engaged with the discharge head 50H that has occupied the separated position to seal and cap the discharge ports 50N of the nozzles of the discharge head 50H. During maintenance, the discharge head 50H performs what is called idle discharge that discharges the posttreatment liquid with the cap part 92B engaged, and the cap part 92B functions as an idle discharge receptacle that receives the posttreatment liquid discharged from the discharge head 50H by this idle discharge. The wiper 93B wipes the posttreatment liquid that has flowed out of the discharge head 50H at the separated position to wipe and clean the discharge head 50H.

The cleaning unit 95B cleans the cap part 92B, the wiper 93B, and the like with the engaging unit 91B returned to a home position after the reciprocation of the engaging unit 91B during maintenance. The cleaning of the engaging unit 91B by the cleaning unit 95B may be regularly performed in other situations such as after image formation with a certain number of sheets.

The maintenance-and-restoration unit 90B includes a pump 96B as a suction unit for suctioning the posttreatment liquid within the discharge head 50H with the cap part 92B engaged with the discharge head 50H at the separated position and causing the posttreatment liquid to flow out of the discharge head 50H. Further, the maintenance-and-restoration unit 90B includes a discharge channel that couples the cap part 92B and the pump 96B to discharge the posttreatment liquid to the outside of the discharge head 50H and a liquid storage that is connected to the discharge channel to store therein the ink and the liquid of the posttreatment liquid that have flowed out of the discharge head 50H.

Figure 8:
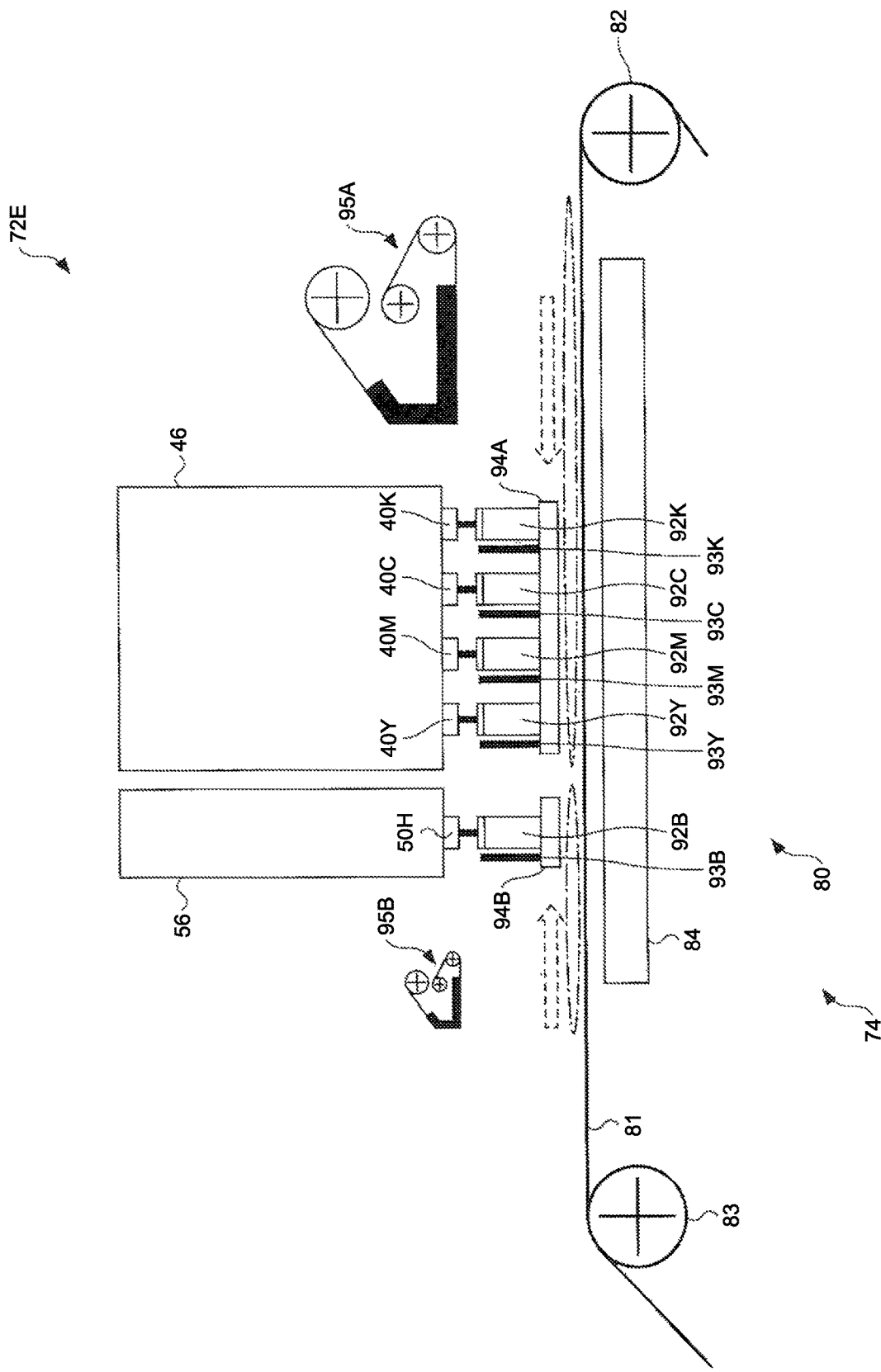
FIG. 8 is a diagram illustrating a maintenance-and-restoration operation of the image forming unit and the posttreatment liquid discharge unit by the maintenance-and-restoration units illustrated in FIG. 7.

FIG. 8 is an illustrative diagram illustrating a maintenance-and-restoration operation of the image forming unit 40 and the posttreatment liquid discharge unit by the maintenance-and-restoration units 90A and 90B. Referring to FIG. 8, this example illustrates how the maintenance-and-restoration operation has been performed using the maintenance-and-restoration units 90A and 90B having the configuration described above. In this case, the image forming unit 40 and the posttreatment unit 50 have moved upward to be at the separated positions, and the engaging units 91A and 91B of the maintenance-and-restoration units 90A and 90B have stopped immediately below the discharge heads 40K, 40C, 40M, and 40Y and the discharge head 50H at the separated positions and have been engaged therewith.

Figure 9:
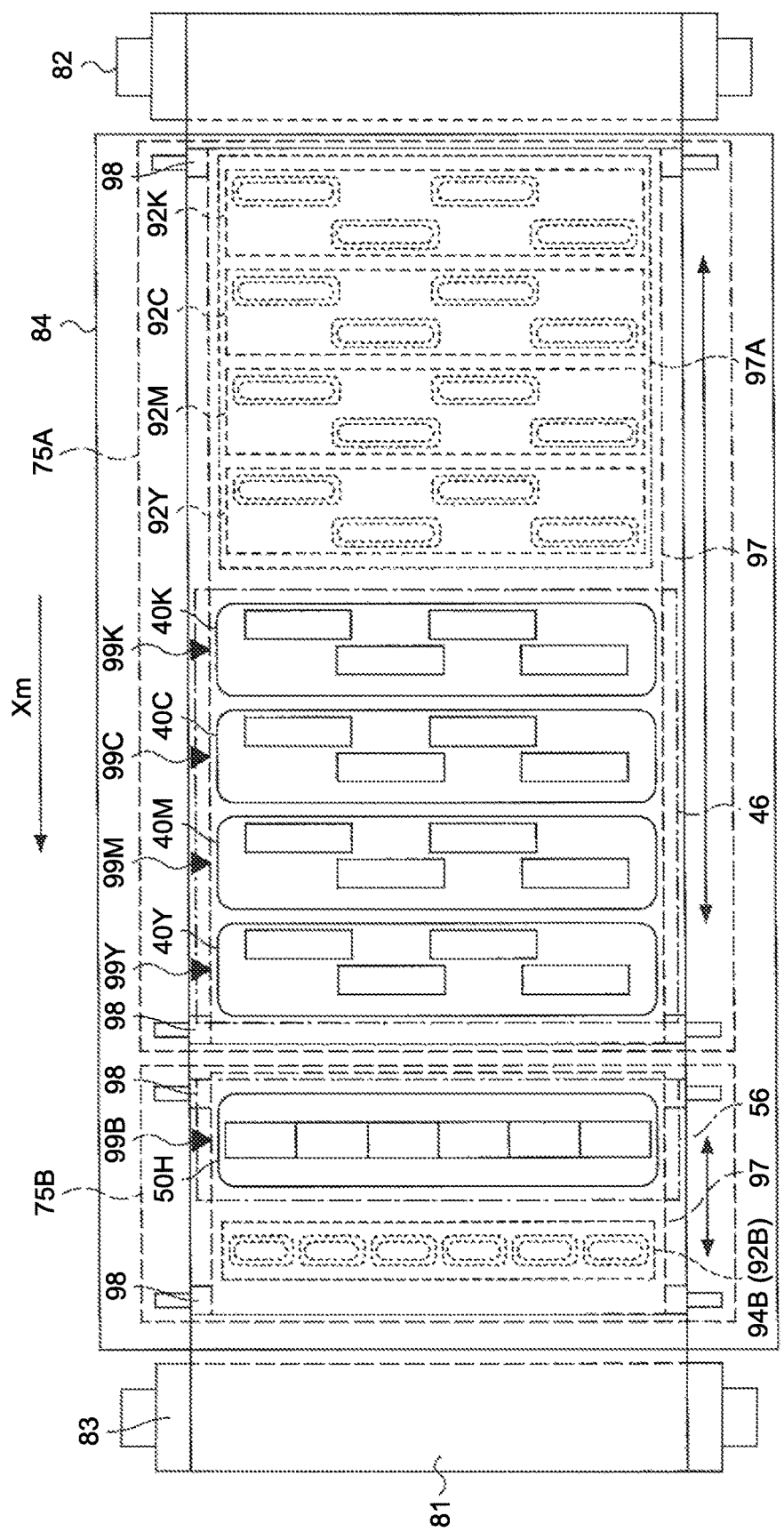
FIG. 9 is a plan view of the image forming unit, the posttreatment liquid discharge unit, and the maintenance-and-restoration units illustrated in FIG. 7.

FIG. 9 is a plan view of the image forming unit 40, the posttreatment liquid discharge unit, and the maintenance-and-restoration units 90A and 90B illustrated in FIG. 7. Referring to FIG. 9, the maintenance-and-restoration unit 90A includes cap parts 92K, 92C, 92M, and 92Y corresponding to the discharge heads 40K, 40C, 40M, and 40Y, respectively, of the image forming unit 40 in a direction perpendicular to the conveyance direction Xm of the rolled paper Md. The maintenance-and-restoration unit 90B includes the cap part 92B.

The maintenance-and-restoration units 90A and 90B include moving units that move the engaging units 91A and 91B. The moving units include reciprocating units 97, 98, 99K, 99C, 99M, and 99Y and reciprocating units 97, 98, and 99B that reciprocate the engaging units 91A and 91B relative to the discharge heads 40K, 40C, 40M, and 40Y and the discharge head 50H. Also included are up-and-down moving units 75A and 75B that support the reciprocating units 97, 98, 99K, 99C, 99M, and 99Y and the reciprocating units 97, 98, and 99B to drive the cap parts 92A and 92B up and down integrally with the engaging units 91A and 91B.

The reciprocating units 97, 98, 99K, 99C, 99M, and 99Y and the reciprocating units 97, 98, and 99B include the following parts. Specifically, included are fixed members 94A and 94B that are integral with the engaging units 91A and 91B, respectively, an endless belt part of which fixes the fixed members 94A and 94B, and two pulleys around which the belt is wound. Also included are position sensors for detecting that the engaging units 91A and 91B are positioned immediately below the discharge heads 40K, 40C, 40M, and 40Y and the discharge head 50H and detect that the engaging units 91A and 91B are positioned at the home position as a position as a starting point of the reciprocation. Further included are a support stage that supports the engaging units 91A and 91B from below in a freely reciprocating manner as described above and a motor as a drive unit that rotatingly drives the pulleys.

Also included is a base member on which a support part including belts as the up-and-down moving units 75A and 75B is mounted and that is arranged and fixed in the upper part with the moving space of the rolled paper Md interposed from the upper face of the casing 74. This base member is connected to a shaft as a drive shaft the lower face part thereof is screwed and a plurality of gears that are fixed to the other end of the shaft and rotate integrally with the shaft, for example. The gears are connected to a stepping motor that rotatingly drives them.

Consequently, as the reciprocating units 97, 98, 99K, 99C, 99M, and 99Y and the reciprocating units 97, 98, and 99B, the motor is driven to rotate the pulleys, whereby the belt can be circulated. With this circulation, the engaging units 91A and 91B can be reciprocated. In this process, the motor is driven so as to cause any of the position sensors to detect the fixed members 94A and 94B. Consequently, the cap parts 92K, 92C, 92M, and 92Y and the cap part 92B can be accurately positioned at a position facing any of the discharge heads 40K, 40C, 40M, and 40Y or the discharge head 50H at the separated positions or the home position.

With the cap parts 92K, 92C, 92M, and 92Y and the cap part 92B positioned, the stepping motor is driven by a certain amount, that is, a certain number of pulses to move the base member upward. With this move, the engaging units 91A and 91B can be moved upward by a certain amount to be engaged with any of the discharge heads 40K, 40C, 40M, and 40Y or the discharge head 50H that has occupied the separated position that the cap parts 92K, 92C, 92M, and 92Y and the cap part 92B face. In place of the stepping motor, a combination of a sensor and a motor that detects the positions of the cap parts 92K, 92C, 92M, and 92Y and the cap part 92B in the up-and-down direction may be used.

In the present embodiment, before maintenance and restoration is performed, a test pattern described below is formed, and a user, a manager, or a serviceman checks the test pattern printed on the rolled paper Md by visual inspection. Only when it is determined that maintenance (cleaning and the like) is required by the visual inspection, the following maintenance-and-restoration operation is performed. Further, in accordance with a result of the visual inspection of the test pattern, maintenance is performed only for a head that requires maintenance.

Specifically, in accordance with the result of the visual inspection of the test pattern, the maintenance-and-restoration operation is performed only for the cap parts 92K, 92C, 92M, and 92Y and the cap part 92B that require maintenance. Further, the maintenance-and-restoration operation can be performed only for a part corresponding to the discharge port 50N of a specific nozzle within the discharge head 50H corresponding to the cap part 92B corresponding to the posttreatment, for example, among these.

The maintenance-and-restoration operation is for the face of the discharge ports 40N of the nozzles of the discharge heads 40K, 40C, 40M, and 40Y of the image forming unit 40 and the face of the discharge ports 50N (not illustrated) of the nozzles of the discharge head 50H of the posttreatment unit 50. Capping is then performed by the cap parts 92K, 92C, 92M, and 92Y and the cap part 92B for discharge. The inks and the posttreatment liquid within the discharge heads 40K, 40C, 40M, and 40Y and within the discharge head 50H are then suctioned by a discharge pump through the cap parts 92K, 92C, 92M, and 92Y and the cap part 92B. Suction sources are the discharge ports 40N of the nozzles of the discharge heads 40K, 40C, 40M, and 40Y or the discharge ports 50N of the nozzles of the discharge head 50H.

After the completion of the suction from the discharge ports 40N of the nozzles or the discharge ports 50N of the nozzles as the maintenance-and-restoration operation, the engaging units 91A and 91B return to the home position. After that, the image forming unit 40 and the posttreatment unit 50 again move downward as before to return to the printing position on the conveying unit 80, reaching a printable state.

In the present embodiment described with reference to FIG. 7 to FIG. 9, the discharge heads 40K, 40C, 40M, and 40Y of the image forming unit 40 and the discharge head 50H of the posttreatment unit 50 are mounted on the carriage 46 and the carriage 56 that are independent from each other. With this configuration, the image forming unit 40 and the posttreatment unit 50 can be maintained at different times.

However, the image forming unit 40 and the posttreatment unit 50 may be integrated to be mounted on the same carriage. In such a configuration, the maintenance-and-restoration units 90A and 90B are also integrated, and the moving mechanism to a maintenance-and-restoration unit 90 is simplified, and the cap parts 92K, 92C, 92M, and 92Y and the cap part 92B are also simplified. In this case, an integrated engaging unit 91 collectively caps the discharge heads 40K, 40C, 40M, and 40Y and the discharge head 50H to perform maintenance and restoration. Consequently, the integrated maintenance-and-restoration units 90A and 90B can be collectively arranged upstream or downstream in the conveyance direction Xm of the rolled paper Md in the image forming unit 40 or the posttreatment unit 50.

The carry-out unit 60 is a unit that carries out the image-formed rolled paper Md. As illustrated in FIG. 1, this carry-out unit 60 in the present embodiment includes a storage unit 61 and a plurality of conveying rollers 62. The carry-out unit 60 winds the image-formed rolled paper Md around a storage roll of the storage unit 61 using the conveying rollers 62 and the like to store therein the image-formed rolled paper Md.

When the rolled paper Md is wound around the storage roll of the storage unit 61, if pressure acting on the rolled paper Md is large, a drying unit that further dries the rolled paper Md immediately before the winding may be provided in order to prevent another image from being transferred to the back face of the rolled paper Md.

Figure 10A:
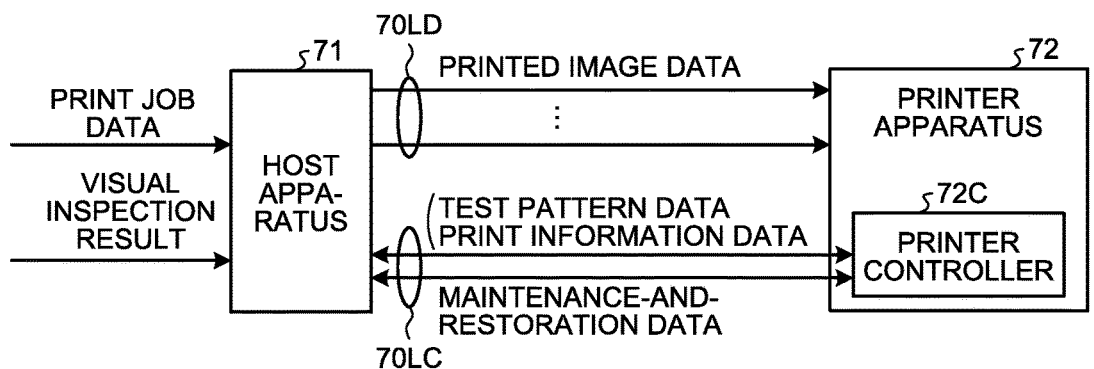
FIG. 10A is a schematic diagram of an overall system configuration of the controller.
Figure 10B:
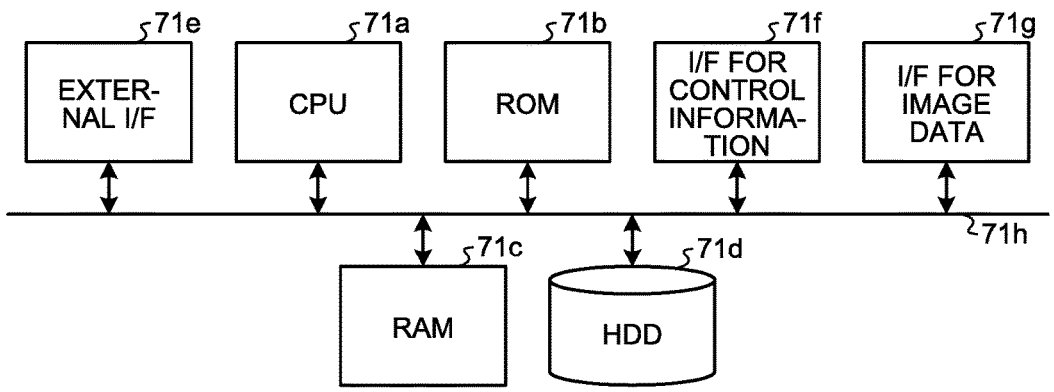
FIG. 10B is a functional block diagram of a detailed configuration of a host apparatus included in the system configuration in FIG. 10A.

FIGS. 10A and 10B are schematic configuration diagrams illustrating an example of the controller 70 to be used in the image forming apparatus 100. FIG. 10A is a schematic diagram of an overall system configuration of the controller 70, and FIG. 10B is a functional block diagram of a detailed configuration of a host apparatus 71 included in the system configuration in FIG. 10A. The controller 70 illustrated in FIG. 10A controls the operation of the image forming apparatus 100 and gives instructions on operations to the components of the image forming apparatus 100 in the present embodiment.

The controller 70 according to the present embodiment may use production printing as a printing system. The production printing is a printable manufacturing system that performs image formation or printing on a large number of image formation media or print objects in a short time by efficiently performing job management, print data management, and the like. Specifically, the controller 70 according to the present embodiment performs raster image processor (RIP) processing that controls the printing operation of bitmap data and the like and printing processing based on the bitmap data and the like controlled by the RIP processing by separate apparatuses.

The controller 70 constructs a system of workflow that performs management from the creation of print data to the distribution of printed objects. In other words, the controller 70 according to the present embodiment separates an apparatus that performs the RIP processing that requires a processing time and an apparatus that performs the printing processing, thereby enabling high-speed printing.

Specifically, as illustrated in FIG. 10A, the controller 70 includes the host apparatus (a digital front end (DFE)) 71 that perform the RIP processing and the like and a printer apparatus 72 that perform the printing processing and the like for the image forming apparatus 100. The host apparatus 71 and the printer apparatus 72 are connected to each other via a plurality of data lines 70LD and a control line 70LC.

The following specifically describes the host apparatus 71 and the printer apparatus 72 included in the controller 70.

The host apparatus 71 of the controller 70 illustrated in FIG. 10A is an apparatus that performs the RIP processing based on print job data containing job data and print data output from a host apparatus. In other words, the host apparatus 71 according to the present embodiment creates pieces of print image data as pieces of bitmap image data corresponding to respective colors based on the print job data. The print image data in the present embodiment further contains data on the discharge of the posttreatment liquid discharged by the posttreatment unit 50, that is, image data on the posttreatment.

The host apparatus 71 according to the present embodiment creates control information data for controlling the printing operation based on the print job data, information from the host apparatus, and the like. This control information data contains data on print form, print type, paper feed/ejection information, print face order, and print sheet size as print conditions, the data size, the resolution, the paper type information, the gray scale, and the color information of the print image data, information on the number of pages to be printed, and the like. The control information data in the present embodiment further contains data on the discharge of the posttreatment liquid discharged by the posttreatment unit 50, that is, control data on the posttreatment.

The user, the manager, the serviceman, or the like inputs the information detected by the visual inspection during maintenance and restoration to the host apparatus 71.

As illustrated in FIG. 10B, the host apparatus 71 in the present embodiment includes a central processing unit (CPU) 71a, a read only memory (ROM) 71b, a random access memory (RAM) 71c, and a hard disk drive (HDD) 71d. The host apparatus 71 also includes an external I/F 71e, an I/F 71f for control information, and an I/F 71g for image data. The I/F is an expression indicating an interface. The host apparatus 71 further includes a bus 71h that connects the CPU 71a and the like. In other words, the host apparatus 71 has a configuration that enables the CPU 71a and the like to perform mutual transmission and reception via the bus 71h.

The CPU 71a controls the operation of the entire host apparatus 71. The CPU 71a controls the operation of the host apparatus 71 using a control program and the like stored in the ROM 71b and the HDD 71d.

The ROM 71b, the RAM 71c, and the HDD 71d all store therein data and the like. The ROM 71b and the HDD 71d store therein a control program for controlling the CPU 71a in advance. The RAM 71c is used as a work memory of the CPU 71a.

The external I/F 71e controls communication concerning transmission and reception with a host apparatus and the like outside the image forming apparatus 100. The I/F 71f for control information controls the communication of the control information data. The I/F 71g for image data controls the communication of the print image data. The I/F 71g for image data in the present embodiment has a plurality of channels described below corresponding to the respective colors of the print image data.

The host apparatus 71 of the controller 70 according to the present embodiment receives the print job data transmitted from the host apparatus by the external I/F 71e and stores the print job data in the HDD 71d using the CPU 71a. The host apparatus 71 reads the print job data from the HDD 71d using the CPU 71a. Further, the host apparatus 71 generates pieces of bitmap data of the respective colors, or yellow Y, cyan C, magenta M, and black K, based on the print job data read using the CPU 71a and stores the generated pieces of bitmap data of the respective colors in the RAM 71c. In this process, the CPU 71a of the host apparatus 71 can generate the pieces of bitmap data of the respective colors by rendering page description language (PDL), for example, as the RIP processing and write out the pieces of bitmap data of the respective colors to the RAM 71c.

Next, the host apparatus 71 compresses and encodes the pieces of bitmap data of the respective colors written out to the RAM 71c and once stores the pieces of encoded bitmap data of the respective colors in the HDD 71d.

Subsequently, when a printing operation is started by the printer apparatus 72, the CPU 71a of the host apparatus 71 reads the pieces of encoded bitmap data of the respective colors from the HDD 71d, decodes the pieces of bitmap data of the respective colors, and writes the pieces of bitmap data of the respective colors in the RAM 71c. Next, the host apparatus 71 reads the pieces of bitmap data of the respective colors from the RAM 71c and outputs the pieces of bitmap data of the respective colors to the printer engine 72E described below of the printer apparatus 72 via the respective channels of the I/F 71g for image data as the pieces of print image data of the respective colors. In this process, the host apparatus 71 can output the pieces of print image data to the printer apparatus 72 via the data lines 70LD illustrated in FIG. 10A as the respective channels of the I/F 71g for image data. These data lines 70LD correspond to data lines 70LD-Y, 70LD-C, 70LD-M, and 70LD-K for the respective colors in FIG. 11 described below.

The host apparatus 71 according to the present embodiment transmits and receives the control information data to and from a printer controller 72C of the printer apparatus 72 using the CPU 71a via the I/F 71f for control information related to the control line 70LC in accordance with the progress of the printing operation and the like.

Further, when the posttreatment is started by the posttreatment unit 50, the host apparatus 71 according to the present embodiment reads encoded image data on the posttreatment from the HDD 71d using the CPU 71a and outputs the encoded image data on the posttreatment to the printer engine 72E via the data line 70LD similarly to the bitmap data. This data line 70LD corresponds to a data line 70LD-P in FIG. 11 described below.

The printer apparatus 72 of the controller 70 is an apparatus that controls operation for performing image formation on the rolled paper Md as the recording medium based on the print image data and the control information data input from the host apparatus 71. The printer apparatus 72 in the present embodiment includes the printer controller 72C and the printer engine 72E illustrated in FIG. 1. As illustrated in FIG. 1, the printer engine 72E includes the casing 73 for conveyance, the casing 74 of the inkjet printer main body, the image forming unit 40, the posttreatment unit 50, the maintenance-and-restoration units 90A and 90B, and the drying unit 30 including the drying unit 32 for posttreatment.

The printer controller 72C controls the operation of the printer engine 72E and transmits and receives the control information data and the like to and from the host apparatus 71 via the control line 70LC. The printer controller 72C transmits and receives the control information data and the like to and from the printer engine 72E via the control line 72LC. With this operation, the printer controller 72C can write print information such as the various kinds of print conditions contained in the control information data and data on a test pattern for discharge in a resistor or the like of a printing controller to store therein the print condition. The printer controller 72C can control the printer engine 72E based on the control information data and perform printing corresponding to the print job data contained in the control information data.

Figure 11:
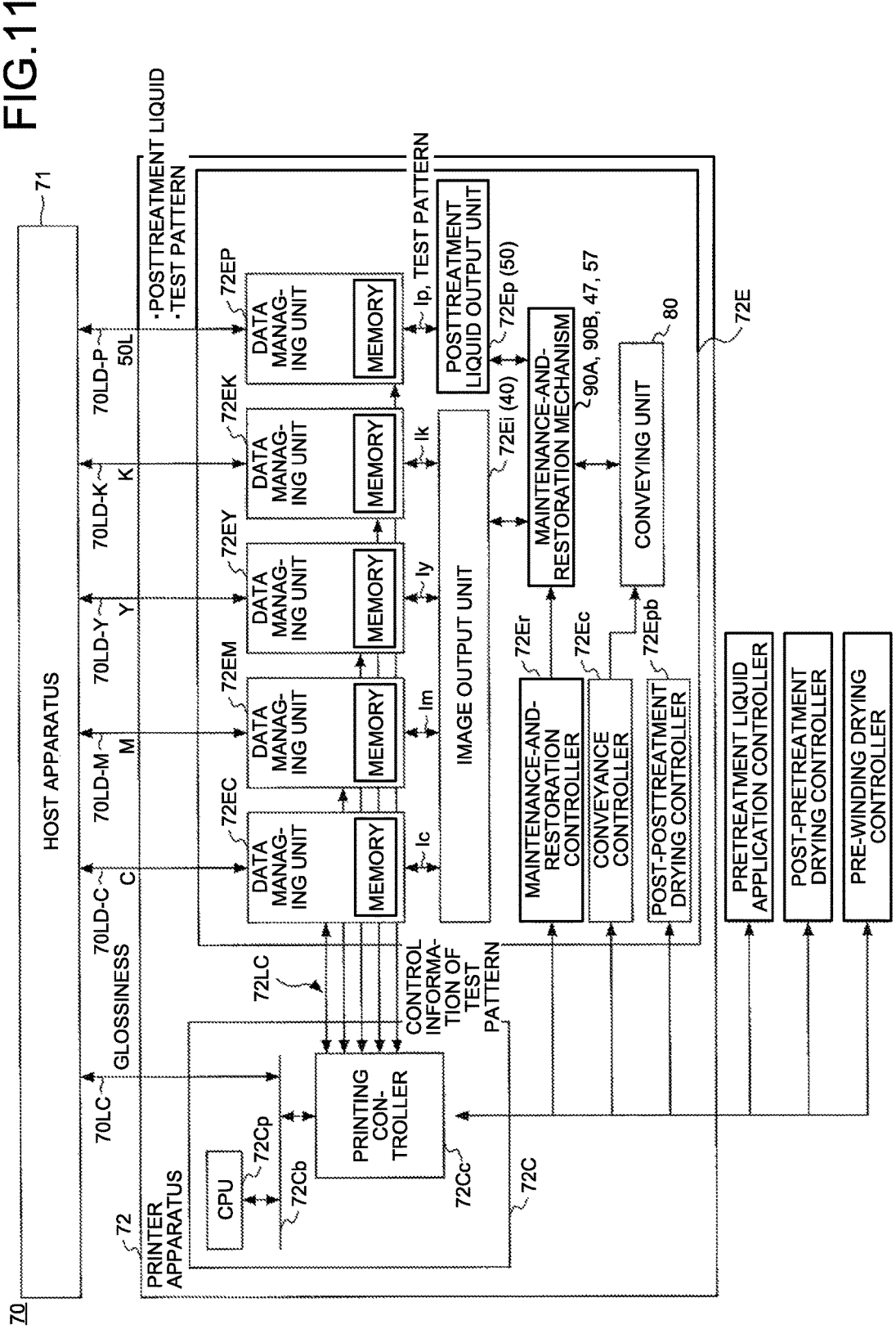
FIG. 11 is a functional block diagram illustrating an example of a basic configuration of the details of the controller illustrated in FIG. 10.

FIG. 11 is a functional block diagram illustrating an example of a basic configuration of the details of the controller 70. Referring to FIG. 11, the printer controller 72C of the printer apparatus 72 in the present embodiment includes a CPU 72Cp and a printing controller 72Cc. The printer controller 72C connects the CPU 72Cp and the printing controller 72Cc in such a manner that they can perform mutual transmission and reception via a bus 72Cb. The bus 72Cb is connected to the control line 70LC via a communication I/F.

The CPU 72Cp controls the operation of the entire printer apparatus 72 using a control program stored in a ROM. The printing controller 72Cc transmits and receives commands and status information to and from the printer engine 72E based on the control information data transmitted from the host apparatus 71. With this operation, the printing controller 72Cc can control the operation of the printer engine 72E.

The printer engine 72E is an apparatus that controls operation to perform image formation on the rolled paper Md based on the print image data input from the host apparatus 71 and the control information data input from the printer controller 72C. The printer engine 72E is an apparatus that controls operation to perform the posttreatment based on the print image data containing the image data on the posttreatment input from the host apparatus 71 and the control information data on the image data on the posttreatment input from the printer controller 72C.

As illustrated in FIG. 11, to the printer engine 72E, the data lines 70LD-Y, 70LD-C, 70LD-M, and 70LD-K for the respective colors and the data line 70LD-P as the data lines 70LD are connected. The printer engine 72E receives the print image data from the host apparatus 71 via the data lines 70LD. With this operation, the printer engine 72E can perform printing operations for the respective colors and the posttreatment with the posttreatment liquid based on the received print image data.

The printer engine 72E in the present embodiment includes a plurality of data managing units 72EC, 72EM, 72EY, and 72EK for the respective colors and a data managing unit 72EP. The printer engine 72E also includes an image output unit 72Ei to which the print image data and the like are input from the data managing unit 72EC and the like and a conveyance controller 72Ec that controls the conveyance of the rolled paper Md. The printer engine 72E in the present embodiment further includes a posttreatment liquid output unit 72Ep to which the image data on the posttreatment is input from the data managing unit 72EP and a post-posttreatment drying controller 72Epb that controls the operation of the drying unit 30. In addition, the printer engine 72E includes a maintenance-and-restoration controller 72Er that controls the operation of a maintenance-and-restoration mechanism including the maintenance-and-restoration units 90A and 90B and the carriage position moving units 47 and 57 described with reference to FIG. 7.

The present embodiment includes a test pattern used in the maintenance-and-restoration operation described below other than during the normal printing as the image data. The printer engine 72E may further include a pretreatment liquid application controller, a post-pretreatment drying controller, and a pre-winding drying controller.

Figure 12:
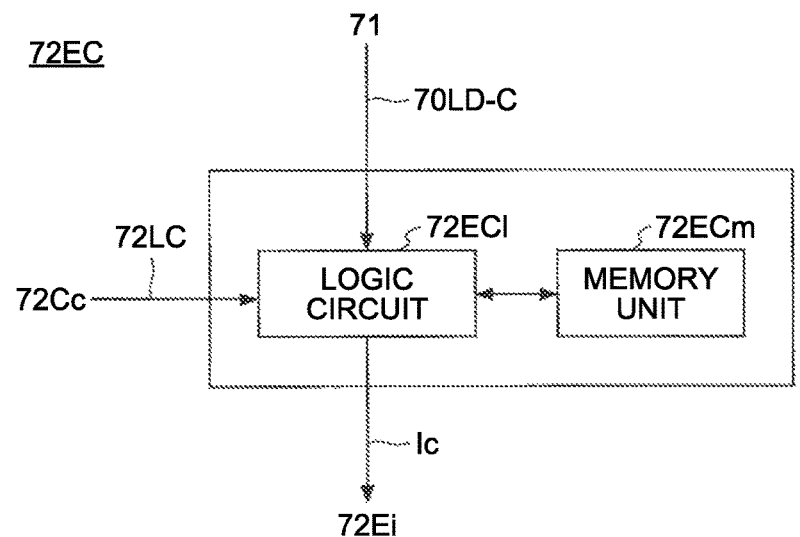
FIG. 12 is a functional block diagram illustrating an example of a detailed configuration of a data managing unit of the controller illustrated in FIG. 11.

FIG. 12 is a functional block diagram illustrating an example of a detailed configuration of the data managing unit 72EC of the controller 70. The configurations of the other data managing units 72EM, 72EY, 72EK, and 72EP are similar to the configuration of the data managing unit 72EC, and descriptions thereof are omitted.

Referring to FIG. 12, the data managing unit 72EC includes a logic circuit 72EC1 and a memory unit 72ECm. The logic circuit 72EC1 of the managing unit 72EC is connected to the host apparatus 71 via the data line 70LD-C. The logic circuit 72EC1 of the managing unit 72EC is connected to the printing controller 72Cc of the printer controller 72C via the control line 72LC.

The logic circuit 72EC1 in the present embodiment stores the print image data output from the host apparatus 71 in the memory unit 72ECm based on a control signal output from the printing controller 72Cc of the printer controller 72C. The logic circuit 72EC1 reads print image data Ic corresponding to cyan C from the memory unit 72ECm based on the control signal output from the printing controller 72Cc of the printer controller 72C and outputs the print image data Ic to the image output unit 72Ei. Concerning the posttreatment, in the case of the data managing unit 72EP of a logic circuit 72ECp, image data Ip on the posttreatment and data for controlling the discharge position of a test pattern for discharge inspection are output to the posttreatment liquid output unit 72Ep.

The memory unit 72ECm can be a capacity that can store therein the print image data at least for three pages. The print image data for three pages indicates the print image data corresponding to a page being received transferred from the host apparatus 71, the print image data corresponding to a page being output to the image output unit 72Ei, and the print image data corresponding to the next page, for example.

For the data managing unit 72EC, a hardware logic circuit including a combination of logic circuits and the like may be used. With this configuration, the data managing unit 72EC can achieve higher-speed processing. The data managing unit 72EC may perform logical determination for a control signal by a bit sequence, for example, using the logic circuit 72EC1 to determine processing to be performed.

Figure 13:
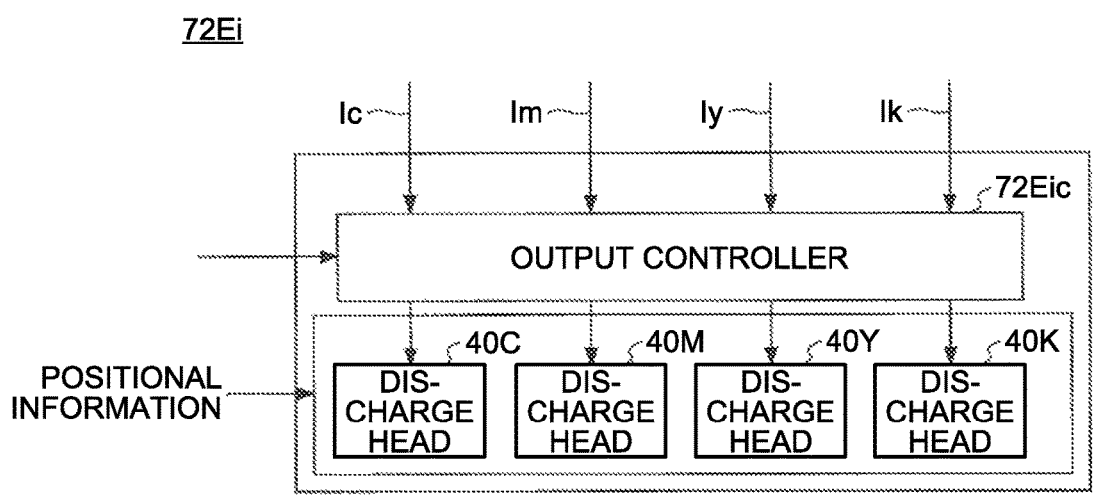
FIG. 13 is a functional block diagram illustrating an example of a detailed configuration of an image output unit of the controller illustrated in FIG. 11.

FIG. 13 is a functional block diagram illustrating an example of a detailed configuration of the image output unit 72Ei of the controller 70. The configuration of the posttreatment liquid output unit 72Ep is basically similar to the configuration of the image output unit 72Ei, and a description thereof is omitted. Referring to FIG. 13, the image output unit 72Ei includes an output controller 72Eic. The output controller 72Eic outputs the pieces of print image data corresponding to the respective colors to the discharge heads 40C, 40M, 40Y, and 40K corresponding to the respective colors. With this operation, the output controller 72Eic can control the operation of the discharge head 40C and the like based on the pieces of print image data.

Specifically, the output controller 72Eic individually controls the discharge head 40C and the like. The output controller 72Eic may simultaneously control the discharge head 40C and the like using the input print image data Ic, for example. Further, the output controller 72Eic may control the discharge head 40C and the like based on a control signal input from a controller. The output controller 72Eic may control the discharge head 40C and the like based on operational input by the user, for example.

As described above, as part of the operation of position moving restoration, by the position moving units, at a time other than during printing, for the purpose of maintenance and restoration, position information is input and controlled so as to cause the image forming unit 40 and the posttreatment unit 50 to move up and down.

From the foregoing, the printer apparatus 72 according to the present embodiment inputs the print image data output from the host apparatus 71 to the discharge head 40C and the like using the data managing unit 72EC and the like and the output controller 72Eic. In this process, the printer apparatus 72 can control the pieces of print image data of the respective colors independently from each other. The printer apparatus 72 can easily change the configuration of the printer engine 72E in accordance with the number of colors of the print image data or the number of the discharge heads 40K, 40C, 40M, and 40Y. In other words, among the data managing unit 72EC and the like and the discharge head 40C and the like, only necessary ones are mounted, thereby producing a favorable effect about the downsizing of the apparatus and cost reduction.

When full-color printing with the four colors is performed, for example, the printer apparatus 72 according to the present embodiment can be provided with all of the data managing unit 72EC and the like in the printer engine 72E.

With this configuration, the printer apparatus 72 can connect the respective pieces of output of the data managing unit 72EC and the like to the discharge head 40C and the like using the output controller 72Eic.

When printing with one color of black K is performed, for example, the printer apparatus 72 can be provided with only one data managing unit 72EK and one discharge head 40K considering apparatus cost priority. With this configuration, the printer apparatus 72 can connect the output of the data managing unit 72EK to the discharge head 40K using the output controller 72Eic.

Alternatively, when printing with one color of black K is performed, for example, one data managing unit 72EK and four discharge heads 40K may be provided considering printing speed priority. With this configuration, the image forming apparatus 100 can connect the output of the data managing unit 72EK to the four discharge heads 40K using the output controller 72Eic. In this case, the image forming apparatus 100 can print the same color, or black K, a plurality of times in a superimposed manner and can achieve image formation with four times higher-speed printing than a case of image formation by one discharge head 40K, for example. The following specifically describes some examples about inspection when discharging the droplets of the ink 40Ink by the image forming unit 40 and discharging the droplets of the posttreatment liquid by the posttreatment unit 50 onto the rolled paper Md being conveyed in the image forming apparatus 100.

Example 1

Figure 14:
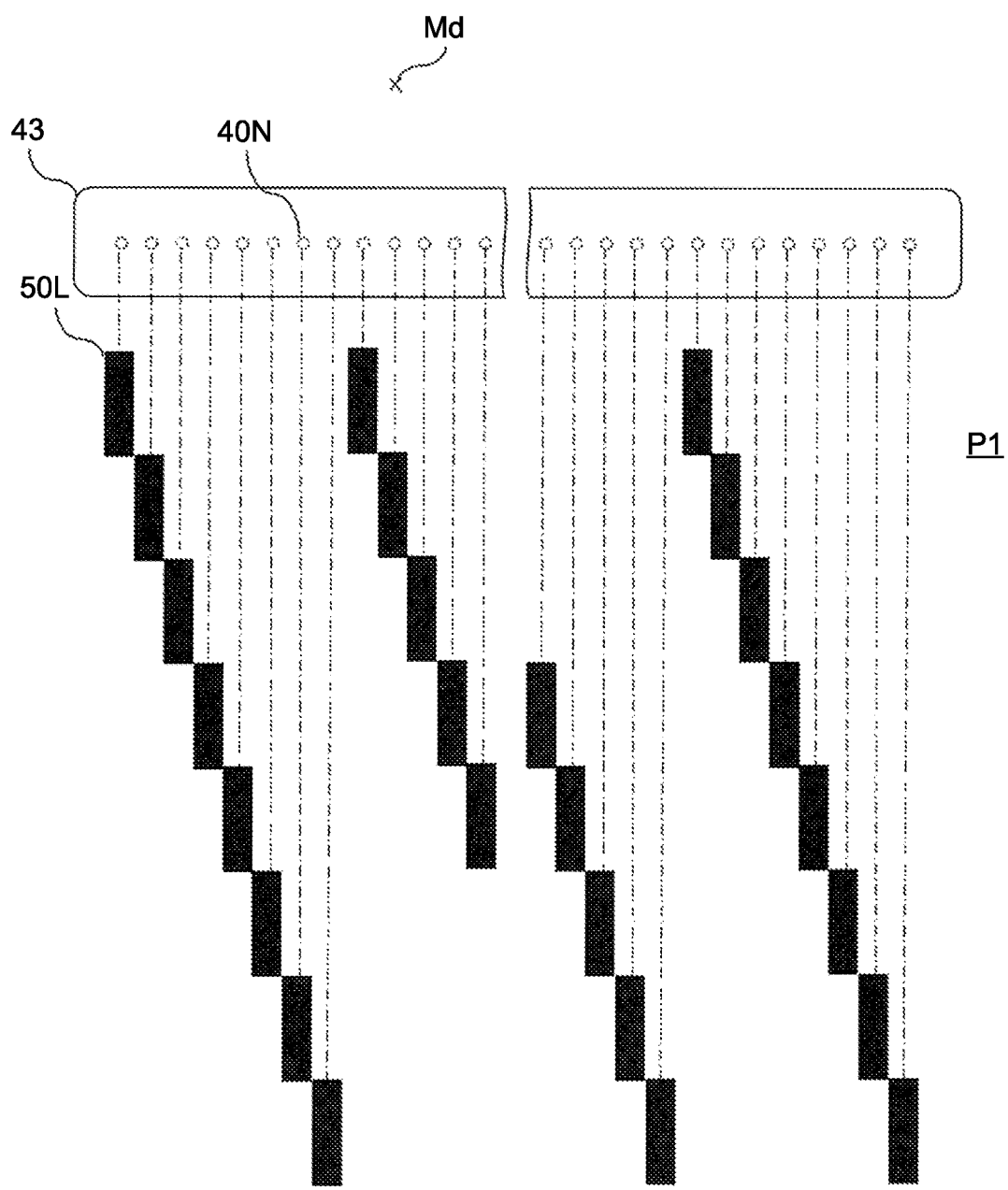
FIG. 14 is a diagram of an example of a test pattern for discharge inspection image-formed on the rolled paper by an image forming apparatus according to Example 1 of the present invention.

FIG. 14 is a diagram of an example of a test pattern P1 for discharge inspection image-formed on the rolled paper Md as the discharged object by the image forming apparatus 100 according to Example 1 of the present invention. In Example 1, the ink 40Ink and the posttreatment liquid are applied to the rolled paper Md by droplet flying by the discharge heads 40K, 40C, 40M, and 40Y and the discharge head 50H that discharge droplets. Before starting printing that performs image formation on the rolled paper Md by this method by droplet flying, abnormal discharge such as the non-discharge or bending of the droplets of the ink 40Ink discharged by the discharge heads 40K, 40C, 40M, and 40Y of the respective colors and the posttreatment liquid discharged by the discharge head 50H is checked. For this purpose, the test pattern P1 for discharge inspection as illustrated in FIG. 14 is printed on the rolled paper Md. This test pattern P1 is image-formed and inspected by discharging the colored droplets of the ink 40Ink from the discharge ports 40N of the nozzles of the discharge heads 40K, 40C, 40M, and 40Y and the transparent droplets 50L of the posttreatment liquid from the discharge ports 50N of the nozzles of the discharge head 50H onto the rolled paper Md.

However, in the case of the posttreatment liquid as the transparent droplets 50L, when the test pattern P1 for discharge inspection is image-formed and printed on the rolled paper Md by the same method, the posttreatment liquid is transparent, and inspection thereon is difficult. This is because the user, the manager, or the serviceman sees reflected light using white light such as natural light to determine recognition details. Specifically, light with respective wavelengths is reflected by the transparent droplets 50L printed on the rolled paper Md, and it is difficult to visually distinguish the reflected light of the rolled paper Md and the reflected light of the transparent droplets 50L from each other. For information, as to light transmittance, the droplets of the transparent posttreatment liquid are higher than the droplets of the four-color ink 40Ink of the respective colors, or black K, cyan C, magenta M, and yellow Y. Consequently, the transparent droplets 50L of the posttreatment liquid can be regarded as an ink with high light transmittance.

Principle

Figure 15:
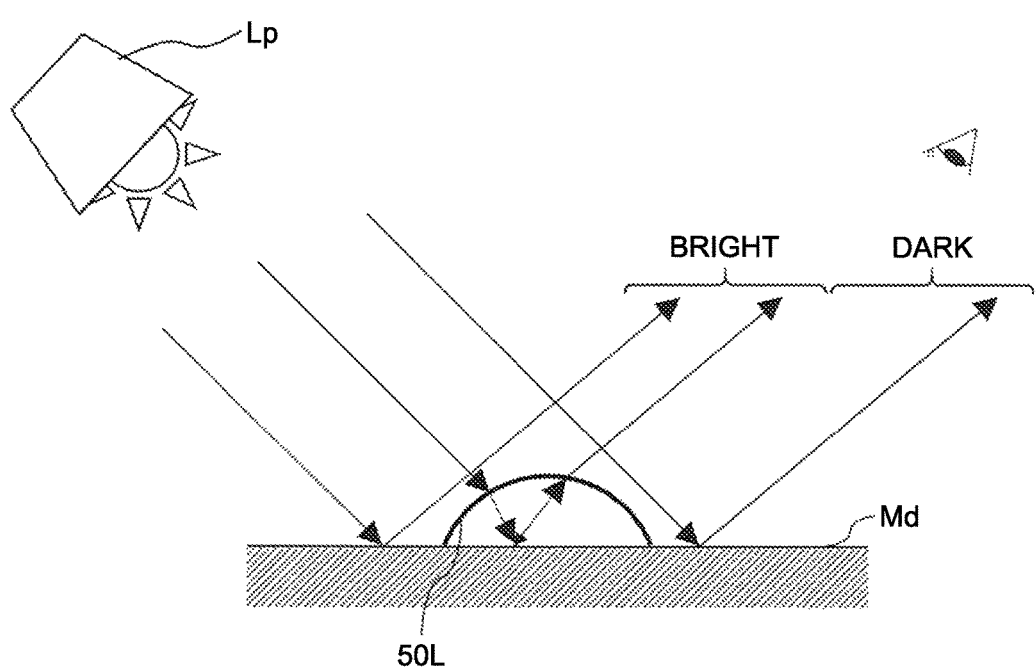
FIG. 15 is a diagram illustrating the detection principle of discharge inspection by an inspection apparatus to be used in the image forming apparatus according to Example 1 of the present invention.

FIG. 15 is a diagram illustrating the detection principle of discharge inspection by an inspection apparatus to be used in the image forming apparatus 100 according to Example 1 of the present invention. Referring to FIG. 15, the inspection apparatus according to Example 1 includes the discharge head 50H of the posttreatment unit 50 as a liquid discharge head that discharges the transparent droplet 50L of the posttreatment liquid onto the rolled paper Md as the discharged object. Also included is a first light source Lp that irradiates the pattern formed by the transparent droplet 50L discharged onto the rolled paper Md with light having a single peak wavelength to cause a difference between brightness and darkness. This example schematically illustrates relation between the transparent droplet 50L image-formed and printed on the rolled paper Md and an optical path and illustrates how the test pattern P1 for discharge inspection has been printed on the rolled paper Md and is being visually inspected. Although this example schematically illustrates how the inspection is visually performed, the test pattern P1 can also be detected by a sensor such as a scanner as described below.

When discharge inspection on the transparent droplet 50L or a light-colored ink is performed, when a light source having a single peak wavelength is used for the first light source Lp, a difference between brightness and darkness occurs. This difference between brightness and darkness is caused by light obtained by narrow-band reflected light that has been reflected simply by the surface of the rolled paper Md other than the transparent droplet 50L and light obtained by the narrow-band reflected light that has passed through the transparent droplet 50L while being reflected and has been reflected by the surface of the rolled paper Md. With this difference between brightness and darkness, the surface of the rolled paper Md and the transparent droplet 50L can be easily distinguished from each other, and discharge detection can be performed by visual inspection or by a sensor such as a scanner as detection principle.

For the light having a single peak wavelength, a red light source (a red light-emitting diode (LED)) with a peak wavelength of 660 nm or a yellow light source (a yellow LED) with a peak wavelength of 590 nm can be used, for example. Such cases also produce a higher effect than a case using white light. Only a single peak wavelength is required, and a laser light source as a single wavelength light source can also be used. Further, the light source that emits light having a single peak wavelength is preferably a light source having a characteristic of a half-value width of 70 nm or less in relative radiation intensity.

Light with a shorter wavelength has a higher refractive index in general, and light reflected within the transparent droplet 50L having a shorter wavelength is easily detected. Specifically, light having a peak wavelength of 570 nm or less is favorable when used for the discharge detection of the transparent droplet 50L. A green light source (a green LED) or a blue light source (a blue LED) may be used, for example. The short wavelength referred to in Example 1 is light having a peak wavelength of 570 nm or less. Examples of the short-wavelength, blue, inexpensive blue light source having a single peak wavelength includes the blue LED. The blue LED is inexpensive and has a shorter wavelength and is favorable when used for the discharge detection of a transparent ink. Consequently, the peak wavelength is preferably in the range of 380 nm to 500 nm.

Thus, the inspection apparatus in Example 1 prints the test pattern P1 for discharge inspection on the rolled paper Md when detecting faulty discharge from the discharge ports 50N of the nozzles of the discharge head 50H that discharge the transparent droplets 50L. Subsequently, for this test pattern P1 for discharge inspection, non-discharge or faulty discharge is detected using the light source having a single peak wavelength.

Example of Scanner

To automatically perform discharge detection inspection on the transparent droplets 50L, for the rolled paper Md on which the transparent droplets 50L have been formed, an image on the rolled paper Md may be read by the scanner 101 provided on the downstream side of the drying unit 30 illustrated in FIG. 1. The state of discharge detection is determined from the image read by the scanner 101. According to this method, the light source of the scanner 101 is the first light source Lp, and the image is read using the light source having a single peak wavelength. In accordance with this procedure, the image is clear, and the determination of the discharge detection inspection is easy. The scanner 101 includes a function as a line-shaped light-receiving sensor Lr that receives light that has been emitted by the line-shaped first light source Lp and has been reflected by the transparent droplets 50L and the rolled paper Md.

For the light source of the scanner 101 itself, there is less need to consider the health of human eyes, and a laser light source can also be used. A UV-LED as a light source having a peak wavelength in the range of 265 nm or more and less than 380 nm known as a shorter-wavelength LED can also be used. However, an LED having a peak wavelength in the range of 265 nm to 340 nm may damage the discharged object such as the rolled paper Md and may be used only when the discharged object is not damaged. Further, when the UV-LED is used, a sensor having sensitivity properties in the range is required to be used as the scanner 101. Sensors having high spectral sensitivity properties in the UV range are known and are not described in detail in this example. Whatever the case may be, when the scanner 101 is used, the first light source Lp having a single peak wavelength in the range of 265 nm to 1,000 nm can be used. The wavelength 1,000 nm is the upper limit of the detection range of the scanner 101.

Figure 17:
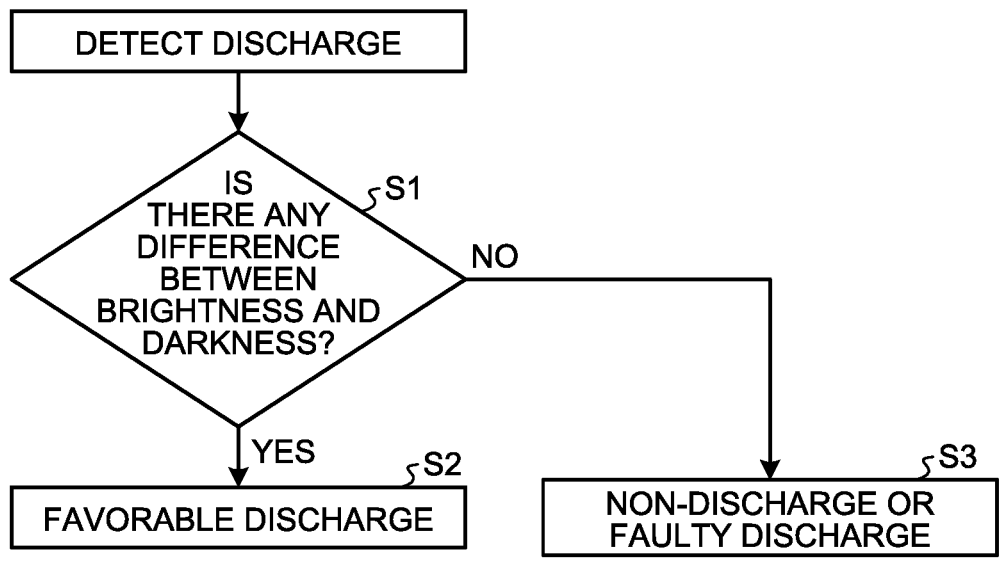
FIG. 17 is a flowchart of the operational principle of discharge detection by a scanner provided in an inspection apparatus for a discharge detection pattern according to Example 1.

FIG. 17 is a flowchart of the operational principle of discharge detection by the scanner 101 provided in an inspection apparatus for a discharge detection pattern according to Example 1. Referring to FIG. 17, in the discharge detection by the scanner 101, first, areas in which the respective colors have been discharged are scanned to acquire image information, and determination whether there is any difference between brightness and darkness in the image information (Step S1) is performed. This presence or absence of the difference between brightness and darkness appears based on a difference between brightness and darkness in the state of reflected light and is determined based on whether the gray scale values of pixels in the image information reach a certain threshold. As a result of this determination, if there is any difference between brightness and darkness, the discharge detection is regarded as being favorable (Step S2), and the process shifts to actual printing. In contrast, if there is no difference between brightness and darkness, the discharge detection is regarded as being non-discharge or faulty discharge (Step S3), and maintenance by the maintenance-and-restoration units 90A and 90B is performed.

Example of Visual Inspection

Figure 19:
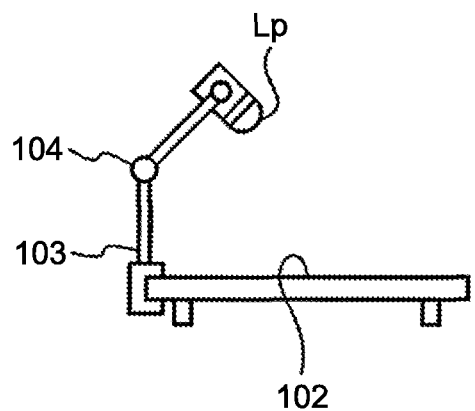
FIG. 19 is a schematic diagram illustrating an example of a basic configuration of an inspection apparatus for visual inspection for the discharge detection pattern according to Example 1.

FIG. 19 is a schematic diagram illustrating an example of a basic configuration of an inspection apparatus for visual inspection for the discharge detection pattern according to Example 1. When the discharge detection inspection on the transparent droplet 50L is performed by visual inspection, an inspection stage 102 as a base separate from the image forming apparatus 100 is used as illustrated in FIG. 19. The first light source Lp may be held on one end of the inspection stage 102 by an illumination mounting tool 103 including an illumination operating unit 104. This first light source Lp forms the inspection apparatus together with the discharge head 50H. A platform truck is mounted on the bottom face of the inspection stage 102 to make the inspection stage 102 travelable. The illumination mounting tool 103 with a link structure is mounted on the inspection stage 102 with another tool such as a clamp, and the first light source Lp is mounted on the tip side of the illumination mounting tool 103. The inspection stage 102 may be foldable type. An operating knob may be used for the illumination operating unit 104. Known techniques can be used for these mounting structures.

For information, although the inspection apparatus that performs the discharge detection inspection by visual inspection has been described as a separate body from the image forming apparatus 100, the inspection stage 102 may be installed at the rear of the image forming apparatus 100 so as to be lowered by one step. Whatever the case may be, as to how the rolled paper Md is brought to the inspection stage 102, if the rolled paper Md is wound around the storage unit 61 of the carry-out unit 60 as illustrated in FIG. 1, an inspector will cut out the rolled paper Md and mount the rolled paper Md on the inspection stage 102. Apart from this, if the image forming apparatus 100 includes a cutter, the rolled paper Md will be cut using it and will be mounted on the inspection stage 102. A structure in which the carry-out unit 60 includes a cutter in place of the winding function to the storage unit 61 is also known, and such a structure may be employed.

When the discharge detection inspection is performed on the transparent droplet 50L by visual inspection, a laser light source and a short-wavelength LED, which may damage human eyes, are not preferably used. Given these circumstances, in the case of visual inspection, a light source having a peak wavelength in the visible range from 375 nm to 780 nm and having certain degree of bandwidth may be used, and an LED light source or an organic EL light source having high color purity can be used, for example. In particular, a violet LED, a blue LED, and a green LED having a peak wavelength in the range of 380 nm to 570 nm are preferable because of easiness of visual inspection. It can be said that the blue LED is optimum, because it generally has a peak wavelength in the range of 450 nm to 500 nm and is available at a low price.

Example of Performing Detection Together with Colored Ink

When the discharge detection inspection on the transparent droplet 50L is performed, when the discharge detection patterns of the colored ink 40Ink are simultaneously printed to perform the discharge detection inspection for each color of the colored ink 40Ink, a time required for the ink discharge detection inspection on all of the heads is reduced, and a time until actual printing is performed is reduced. The colored ink 40Ink indicates having colors that can be easily visually inspected or detected under a white light source. Specifically, the colored ink 40Ink indicates inks of process colors such as black K, cyan C, magenta M, and yellow Y and special inks such as pink and orange.

Figure 16:
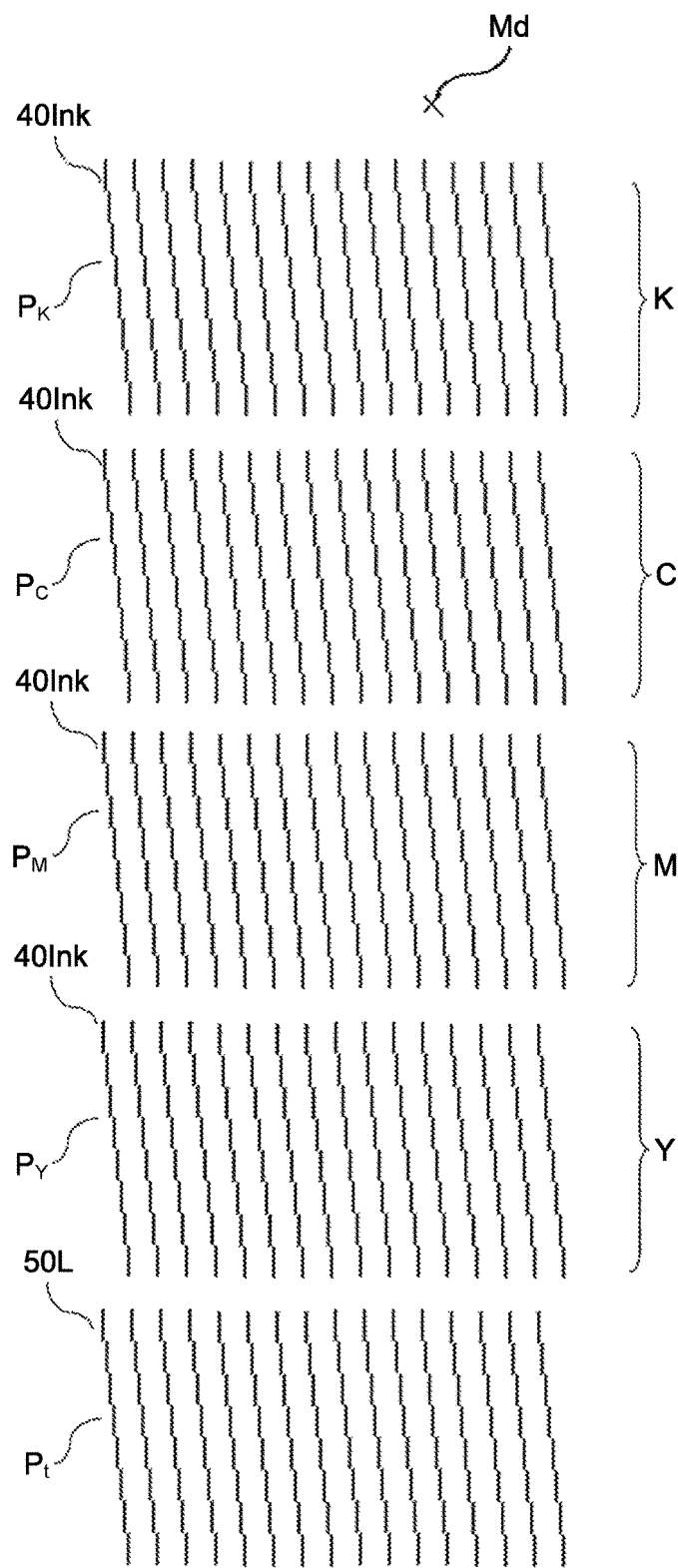
FIG. 16 is a diagram of discharge detection patterns when discharge detection inspection is performed together with colored inks by the inspection apparatus according to Example 1.

FIG. 16 is a diagram of discharge detection patterns when discharge detection inspection is performed together with colored inks by the inspection apparatus according to Example 1. This example illustrates how discharge detection patterns PK, PC, PM, PY, and Pt have been image-formed and printed for each color in the discharge heads 40K, 40C, 40M, and 40Y for the respective colors to be used and the discharge head 50H for the posttreatment liquid on the rolled paper Md. The colored ink 40Ink can be visually inspected or detected under a white light source, and the white light source may be provide separately, and the discharge detection inspection may be performed under the white light source. When the discharge detection inspection on the transparent droplet 50L is performed, the white light source is switched to a light source having a single peak wavelength, whereby the discharge detection inspection can be appropriately performed on the colored ink 40Ink and the transparent droplet 50L.

When non-discharge is detected from these printed discharge detection patterns PK, PC, PM, PY, and Pt, when light of a color that is low in the spectral reflectance properties of the colored ink 40Ink that has formed the discharge detection patterns PK, PC, PM, PY, and Pt is emitted, visual inspection or detection is performed more easily. Given this situation, a second light source Lp' that emits light of the color corresponding to a region that is low in the spectral reflectance properties of this colored ink 40Ink is preferably provided.

The Ink 40Ink of magenta M is easily detected when a green LED having a peak wavelength of 500 nm to 570 nm is emitted, for example. Similarly, the ink 40Ink of cyan C is easily detected when a red LED having a peak wavelength of 600 nm to 700 nm is emitted. The ink 40Ink of yellow Y is easily detected when a green light source having a peak wavelength of 450 nm to 500 nm is emitted. For the discharge detection inspection on the transparent droplet 50L, a blue LED can be used, for example. The color that is low in the spectral reflectance properties of the colored ink 40Ink can also be referred to as a complementary color, and the light of the respective colors can also be referred to as a complementary color light source.

Figure 18:
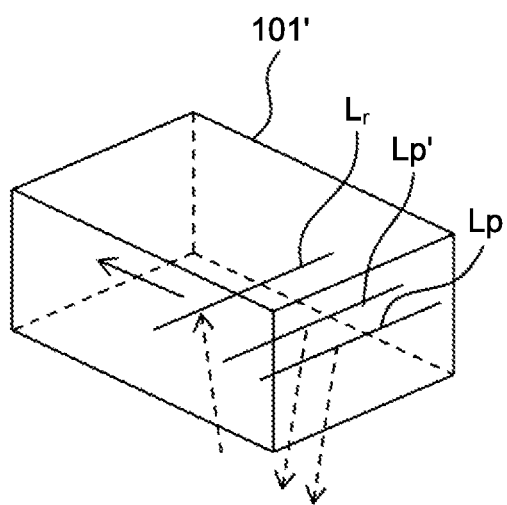
FIG. 18 is a schematic diagram illustrating a basic configuration according to another example of an inspection apparatus for automatic operation for the discharge detection pattern according to Example 1.
Figure 20:
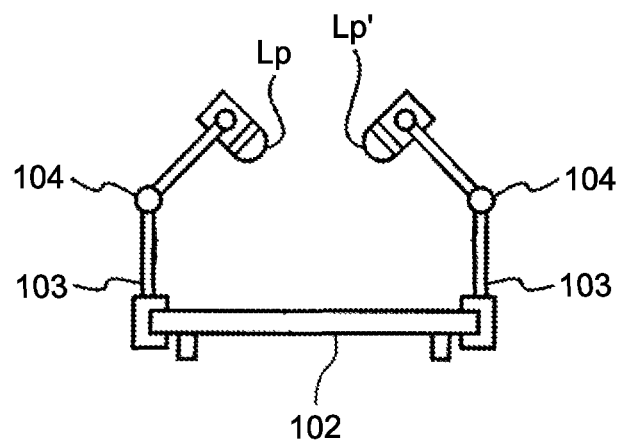
FIG. 20 is a schematic diagram illustrating another example of the basic configuration of the inspection apparatus for visual inspection for the discharge detection pattern according to Example 1.

FIG. 18 is a schematic diagram illustrating a basic configuration according to another example of an inspection apparatus for automatic operation for the discharge detection pattern according to Example 1. A scanner 101' in this example also includes the line-shaped second light source Lp' that emits light of the color in the area having low spectral reflectance properties of the colored ink 40Ink in addition to the line-shaped first light source Lp. The functions as the line-shaped light-receiving sensor Lr also receives light that has been emitted by the second light source Lp' and has been reflected by the transparent droplet 50L or the rolled paper Md in addition to the first light source Lp. The second light source Lp' may be a plurality of light sources and may be a light source that can switch among a plurality of colors. The first light source Lp, the second light source Lp', and the light-receiving sensor Lr are all arranged in a line shape and scan the rolled paper Md in the conveyance direction Xm while maintaining a certain spacing. To automatically perform the discharge detection inspection on the colored ink 40Ink and the transparent droplet 50L, as to the discharge detection patterns PK, PC, PM, PY, and Pt of the respective colors, the images on the rolled paper Md may be read by the scanner 101' illustrated in FIG. 18. With the first light source Lp and the second light source Lp' as the light sources of the scanner 101', the images of the discharge detection patterns PK, PC, PM, PY, and Pt of the respective colors are read while switching between the blue light source for the transparent droplet 50L and the light source of the color that is low in the spectral reflectance properties for the colored ink 40Ink as described above. For information, as another example of the inspection apparatus for visual inspection, as illustrated in FIG. 20, the second light source Lp' may be separately mounted on the inspection stage 102 by a mounting structure similar to the one described with reference to FIG. 19. In this inspection apparatus, the second light source Lp' is held by the illumination mounting tool 103 including the illumination operating unit 104 on the side facing the first light source Lp.

The spectral reflectance properties of the ink of yellow Y is as low as 450 nm to 500 nm, and when the discharge detection pattern Pt of the transparent droplet 50L is printed before or after the discharge detection pattern of the ink of yellow Y as illustrated in FIG. 16 to perform the discharge detection inspection, all that is required is to emit the same blue LED when the discharge detection inspection is performed. Such being the case, the first light source Lp and the second light source Lp' of light source emission are not required to be switched between the ink of yellow Y and the transparent droplet 50L. In addition, the images can be read simultaneously, and an inspection time is reduced.

Example 2

Figure 21:
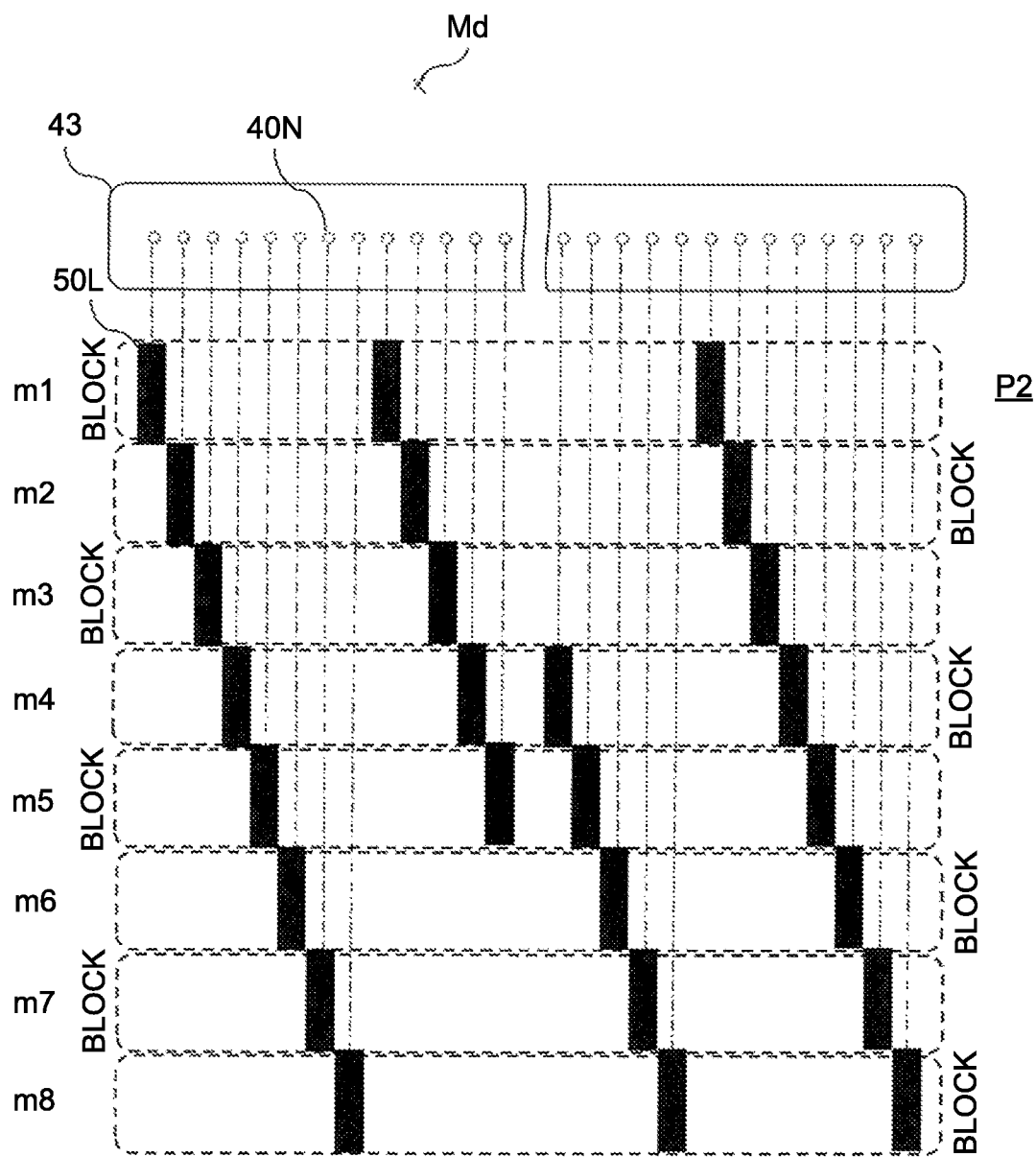
FIG. 21 is a diagram of an example of a test pattern for discharge inspection image-formed on the rolled paper by an image forming apparatus according to Example 2 of the present invention.

FIG. 21 is a diagram of an example of a test pattern P2 for discharge inspection image-formed on the rolled paper Md by an image forming apparatus according to Example 2 of the present invention. Also in Example 2, the ink 40Ink and the posttreatment liquid are applied to the rolled paper Md by droplet flying by the discharge heads 40K, 40C, 40M, and 40Y and the discharge head 50H that discharge droplets. Before starting printing that performs image formation on the rolled paper Md by this method by droplet flying, abnormal discharge such as non-discharge or bending of the droplets of the ink 40Ink discharged by the discharge heads 40K, 40C, 40M, and 40Y of the respective colors and the posttreatment liquid discharged by the discharge head 50H is checked. For this purpose, the test pattern P2 for discharge inspection as illustrated in FIG. 18 is printed on the rolled paper Md.

This test pattern P2 for discharge inspection has been image-formed and printed by setting the nozzle rows of the discharge heads 40K, 40C, 40M, and 40Y and the discharge head 50H. The discharge head 50H includes a first nozzle row that discharges the transparent droplets 50L while moving in a first direction relative to the rolled paper Md. The discharge heads 40K, 40C, 40M, and 40Y include a second nozzle row in which the discharge ports 40N of a plurality of nozzles are arranged in a second direction orthogonal to the first direction. The test pattern P2 for discharge inspection is formed to have m (m is a natural number of 2 or more) pattern rows arranged in the first direction, the patterns in each of the m pattern rows being arranged with an interval of (m−1). In FIG. 21, the number of pattern rows m is 8, and in each of the pattern rows, the patterns are arranged with an interval of 7, for example.

This test pattern P2 for discharge inspection has been image-formed and printed by discharging the ink 40Ink as the colored droplets from the discharge ports 40N of the nozzles of the discharge heads 40K, 40C, 40M, and 40Y onto the rolled paper Md. However, in the case of the transparent droplets 50L, when the test pattern P2 for discharge inspection is printed on the rolled paper Md from the discharge ports 50N of the nozzles of the discharge head 50H by the same method, being transparent makes the inspection difficult. This fact is as described in Example 1.

When the discharge inspection is performed by printing the test pattern P2 for discharge inspection on the rolled paper Md, treatment similar to that of Example 1 described with reference to FIG. 15 is performed. Also in Example 2, similarly to Example 1, when faulty discharge from the discharge ports 50N of the respective nozzles of the discharge head 50H of the transparent droplets 50L is detected, the transparent droplets 50L are discharged from the discharge head 50H onto the rolled paper Md to print the test pattern P2. Subsequently, the transparent droplet 50L of the test pattern P2 is irradiated with light having a single peak wavelength by the first light source Lp, and non-discharge or faulty discharge of each of the nozzles of the discharge head 50H is detected from the state of brightness and darkness of its reflected light. Using a light source that emits light having a single peak wavelength to cause a difference between brightness and darkness as the first light source Lp and the use of the blue LED being preferable are also similar to Example 1.

Also in Example 2, when the discharge detection of the transparent droplet 50L is performed, printing the test pattern P2 for the discharge inspection of the colored ink 40Ink simultaneously and performing the discharge detection for each ink color are also similar to Example 1 described with reference to FIG. 16. The configuration of the inspection apparatus when performing the discharge inspection on the colored ink 40Ink and the transparent droplet 50L automatically or by visual inspection or the procedure when the discharge inspection is performed by switching the light source for the respective colors including the case of using the second light source Lp' are also similar to Example 1, producing a similar effect. In Example 2, the test pattern P2 is as illustrated in FIG. 21, which is suitable for detection by visual inspection.

The technical essence of the inspection apparatus described in the examples can be described as a method of inspection. This method of inspection includes a liquid discharge step that discharges a transparent liquid onto a discharged object from a liquid discharge head and a light irradiation step that irradiates a pattern formed by the transparent liquid discharged onto the discharged object at the liquid discharge step with light having a single peak wavelength from a first light source to cause a difference between brightness and darkness. The light having a single peak wavelength can be selected from being light having a peak wavelength in the wavelength range of 265 nm to 1,000 nm and being light having a peak wavelength in the wavelength range of 375 nm to 780 nm. The light having a single peak wavelength can also be selected from being light having a peak wavelength in the wavelength range of 380 nm to 570 nm and being light having a peak wavelength in the wavelength range of 450 nm to 500 nm. Whatever the case may be, an inspection step is preferably included that inspects the non-discharge or faulty discharge of the liquid discharge head based on the state of reflection light reflected by the transparent liquid and parts other than that. The state of the reflected light preferably appears as a difference between brightness and darkness.

According to these examples, when the faulty discharge of the transparent droplet 50L is detected, the test patterns P1 and P2 are irradiated with the light having a single peak wavelength by the first light source Lp to cause a difference between brightness and darkness. Consequently, the faulty discharge of the transparent droplet 50L can be appropriately detected from the relation of brightness and darkness without using the colored ink 40Ink. In addition, there is no influence of the non-discharge or bent discharge of the colored ink 40Ink, and the accuracy of detecting the non-discharge of the transparent droplet 50L increases. Further, maintenance for making the non-discharge or bent discharge of the colored ink 40Ink normal discharge is eliminated, and a time and an amount of ink used required therefor can be reduced.

According to an aspect of the embodiments, it is possible to appropriately detect the faulty discharge of a liquid discharge head that discharges a transparent liquid onto a discharged object. Objects other than described above, configurations, and effects will be clarified by the following description of the embodiments.

The above-described embodiments are illustrative and do not limit the present invention. Thus, numerous additional modifications and variations are possible in light of the above teachings. For example, at least one element of different illustrative and exemplary embodiments herein may be combined with each other or substituted for each other within the scope of this disclosure and appended claims. Further, features of components of the embodiments, such as the number, the position, and the shape are not limited the embodiments and thus may be preferably set. It is therefore to be understood that within the scope of the appended claims, the disclosure of the present invention may be practiced otherwise than as specifically described herein.

The method steps, processes, or operations described herein are not to be construed as necessarily requiring their performance in the particular order discussed or illustrated, unless specifically identified as an order of performance or clearly identified through the context. It is also to be understood that additional or alternative steps may be employed.

Further, as described above, any one of the above-described and other methods of the present invention may be embodied in the form of a computer program stored in any kind of storage medium. Examples of storage mediums include, but are not limited to, flexible disk, hard disk, optical discs, magneto-optical discs, magnetic tapes, non-volatile memory, semiconductor memory, read-only-memory (ROM), etc.

Alternatively, any one of the above-described and other methods of the present invention may be implemented by an application specific integrated circuit (ASIC), a digital signal processor (DSP) or a field programmable gate array (FPGA), prepared by interconnecting an appropriate network of conventional component circuits or by a combination thereof with one or more conventional general purpose microprocessors or signal processors programmed accordingly.

Each of the functions of the described embodiments may be implemented by one or more processing circuits or circuitry. Processing circuitry includes a programmed processor, as a processor includes circuitry. A processing circuit also includes devices such as an application specific integrated circuit (ASIC), digital signal processor (DSP), field programmable gate array (FPGA) and conventional circuit components arranged to perform the recited functions.

What is claimed is:
1. An inspection apparatus comprising:
    a liquid discharge head configured to discharge a transparent liquid onto a discharged object; and a first light source configured to irradiate a pattern formed by the transparent liquid discharged onto the discharged object with light having a single peak wavelength to cause a difference between brightness and darkness.

2. The inspection apparatus according to claim 1, wherein the first light source emits light having the peak wavelength within a wavelength range of 265 nm to 1,000 nm.

3. The inspection apparatus according to claim 2, wherein the first light source emits light having the peak wavelength within a wavelength range of 375 nm to 780 nm.

4. The inspection apparatus according to claim 3, wherein the first light source emits light having the peak wavelength within a wavelength range of 380 nm to 570 nm.

5. The inspection apparatus according to claim 4, wherein the first light source emits light having the peak wavelength within a wavelength range of 450 nm to 500 nm.

6. The inspection apparatus according to claim 1, wherein the first light source is a light-emitting diode (LED) light source.

7. The inspection apparatus according to claim 1, wherein
the transparent liquid or the discharged object reflects light that has been emitted by the first light source, and
the inspection apparatus further comprises a sensor configured to receive the reflected light.

8. The inspection apparatus according to claim 1, further comprising a second light source configured to irradiate a pattern formed by a colored liquid discharged onto the discharged object with light of a color corresponding to a region that is low in spectral reflection intensity of the liquid.

9. The inspection apparatus according to claim 1, wherein
the liquid discharge head is a recording head including a first nozzle row and a second nozzle row, the first nozzle row being configured to move in a first direction relative to the discharged object, the second nozzle row including a plurality of nozzles arranged in a second direction orthogonal to the first direction, and
the pattern formed has m pattern rows arranged in the first direction, patterns included in each of the m pattern rows being arranged with an interval of (m-1), where m is a natural number of 2 or more.

10. A method of inspection comprising:
discharging a transparent liquid from a liquid discharge head onto a discharged object; and
irradiating a pattern formed by the transparent liquid discharged onto the discharged object at the discharging with light having a single peak wavelength from a first light source to cause a difference between brightness and darkness.

11. The method of inspection according to claim 10, wherein the light having a single peak wavelength is light having the peak wavelength within a wavelength range of 265 nm to 1,000 nm.

12. The method of inspection according to claim 11, wherein the light having a single peak wavelength is light having the peak wavelength within a wavelength range of 375 nm to 780 nm.

13. The method of inspection according to claim 12, wherein the light having a single peak wavelength is light having the peak wavelength within a wavelength range of 380 nm to 570 nm.

14. The method of inspection according to claim 13, wherein the light having a single peak wavelength is light having the peak wavelength within a wavelength range of 450 nm to 500 nm.

15. The method of inspection according to claim 10, further comprising inspecting non-discharge or faulty discharge of the liquid discharge head based on a state of reflected light reflected from the transparent liquid and parts other than the transparent liquid.

16. The method of inspection according to claim 15, wherein the state of the reflected light appears as the difference between brightness and darkness.

* * * * *